US012660986B2

(12) United States Patent
Bagley et al.

(10) Patent No.: US 12,660,986 B2
(45) Date of Patent: Jun. 23, 2026

(54) REPOSITIONABLE TISSUE-ENGAGEMENT MEMBER AND ASSOCIATED SYSTEMS AND METHODS

(71) Applicants: BOSTON SCIENTIFIC SCIMED, INC., Maple Grove, MN (US); BOSTON SCIENTIFIC MEDICAL DEVICE LIMITED, Galway (IE)

(72) Inventors: Kevin L. Bagley, Natick, MA (US); Deepak Kumar Sharma, Muzaffarnagar (IN); Shrikant Vasant Raut, Mumbai (IN); James J. Scutti, Norwell, MA (US); Agrim Mishra, New Delhi (IN); Nabarun Bhowmick, Kolkata (IN)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 555 days.

(21) Appl. No.: 17/735,646

(22) Filed: May 3, 2022

(65) Prior Publication Data

US 2022/0354345 A1 Nov. 10, 2022

Related U.S. Application Data

(60) Provisional application No. 63/183,790, filed on May 4, 2021.

(51) Int. Cl.
*A61B 1/00* (2006.01)
*A61B 1/04* (2006.01)
(Continued)

(52) U.S. Cl.
CPC .......... *A61B 1/00087* (2013.01); *A61B 1/042* (2013.01); *A61B 2017/00269* (2013.01);
(Continued)

(58) Field of Classification Search
CPC . A61B 17/128; A61B 17/1285; A61B 17/083; A61B 17/02; A61B 17/10
See application file for complete search history.

(56) References Cited

U.S. PATENT DOCUMENTS 5,569,274 A 10/1996 Rapacki et al.
7,081,121 B2 * 7/2006 Muramatsu ........ A61B 17/1227
606/139

(Continued)

FOREIGN PATENT DOCUMENTS

CN 109620320 A 4/2019
CN 209422007 U 9/2019
(Continued)

OTHER PUBLICATIONS

New Monopolar Flexible Endoscopic Scissors with Patented Edge Flex™ Technology, Slater Endoscopy Enzisor Endoscopic Scissors, pp. 1-6, Jul. 7, 2022.
(Continued)

*Primary Examiner* — Elizabeth Houston
*Assistant Examiner* — Serenity A Miller
(74) *Attorney, Agent, or Firm* — Seager, Tufte & Wickhem, LLP

(57) ABSTRACT

A tissue-engagement member having a pair of jaws movable between a closed configuration and an open configuration, an actuator movable to shift the jaws between the closed and open configurations, and a biasing element biasing the jaws into a closed configuration. The biasing element may be provided over a portion of the tissue-engagement member. A cam mechanism may be provided in operative association with at least one of the jaws and/or the actuator. The biasing element may operatively engage at least one of the jaws and/or the actuator to actuate the cam mechanism to return the jaws to a closed configuration from an open configuration. A manipulator having an actuator-engagement element (Continued)

may be provided to engage an actuation element operatively associated with the actuator. The actuator-engagement element may operatively engage the actuation element in a range of orientations.

19 Claims, 14 Drawing Sheets

(51) Int. Cl.
| | |
|---|---|
| *A61B 17/00* | (2006.01) |
| *A61B 17/22* | (2006.01) |
| *A61B 17/29* | (2006.01) |
| *A61B 18/00* | (2006.01) |

(52) U.S. Cl.
CPC ............... *A61B 2017/22034* (2013.01); *A61B 2017/2933* (2013.01); *A61B 2018/00601* (2013.01)

(56) References Cited

U.S. PATENT DOCUMENTS

| | | | |
|---|---|---|---|
| 7,166,570 | B2 | 1/2007 | Hunter et al. |
| 8,852,088 | B2 | 10/2014 | Ransden et al. |
| 9,694,082 | B2 | 7/2017 | Kaplan et al. |
| 9,974,532 | B2 | 5/2018 | Baas et al. |
| 9,999,415 | B2 | 6/2018 | Duan et al. |
| 10,694,934 | B2 | 6/2020 | Wales et al. |
| 10,905,411 | B2* | 2/2021 | Racenet ............. A61B 17/0469 |
| 2003/0130669 | A1* | 7/2003 | Damarati .......... A61B 17/0401 606/232 |
| 2005/0080440 | A1* | 4/2005 | Durgin ................. A61B 17/122 606/151 |
| 2005/0107809 | A1* | 5/2005 | Litscher ............. A61B 17/1285 606/142 |
| 2012/0016391 | A1* | 1/2012 | Aguirre ................. A61B 17/10 606/151 |
| 2014/0135820 | A1 | 5/2014 | Schaller et al. |
| 2014/0243586 | A1* | 8/2014 | Rohaninejad .......... A61B 34/73 600/37 |
| 2016/0354101 | A1* | 12/2016 | Melsheimer ........... A61B 17/29 |
| 2018/0035997 | A1* | 2/2018 | Smith ............. A61B 17/00234 |
| 2018/0263614 | A1* | 9/2018 | Lee .................... A61B 17/0218 |
| 2018/0272033 | A1 | 9/2018 | Hoang et al. |
| 2019/0033672 | A1 | 1/2019 | Ohori |
| 2019/0059905 | A1* | 2/2019 | Adams ............... A61B 17/1285 |
| 2019/0099172 | A1 | 4/2019 | Wales et al. |
| 2019/0231352 | A1 | 8/2019 | Maekubo |
| 2019/0336728 | A1* | 11/2019 | Unger ................ A61B 17/0218 |
| 2020/0129181 | A1 | 4/2020 | Carrillo, Jr. et al. |
| 2020/0360023 | A1 | 11/2020 | Bagley et al. |
| 2022/0054156 | A1* | 2/2022 | Tang .................. A61B 17/1285 |

FOREIGN PATENT DOCUMENTS

| | | |
|---|---|---|
| CN | 110944588 A | 3/2020 |
| CN | 210541656 U | 5/2020 |
| CN | 210541727 U | 5/2020 |
| EP | 3097871 A1 | 11/2016 |
| EP | 3689254 A1 | 8/2020 |
| JP | H0970405 A | 3/1997 |
| JP | 2007097663 A | 4/2007 |
| JP | 2007159794 A | 6/2007 |
| JP | 2008062004 A | 3/2008 |
| JP | 2015192726 A | 11/2015 |
| JP | 2019154465 A | 9/2019 |
| JP | 2019154978 A | 9/2019 |
| JP | 2019162259 A | 9/2019 |
| KR | 101340661 B1 | 12/2013 |
| WO | 9600033 A1 | 1/1996 |
| WO | 2021000782 A1 | 1/2021 |

OTHER PUBLICATIONS

Gulka et al., "A Novel Silk-based Vocal Fold Augmentation Material: 6-month Evaluation In A Canine Model", p. 1, 2018.

Brown et al., "Injectable Silk-based Biomaterials For Cervical Tissue Augmentation: an in vitro study", pp. 1-2, 2016.

Vepari et al., "Silk As A Biomaterial", pp. 1-25, 2007.

Spotnitz, "Fibrin Sealant: The Only Approved Hemostat, Sealant, and Adhesive—A Laboratory and Clinical Perspective", vol. 2014, Article ID 203943, pp. 1-29, 2014.

Patentability Search Results_20-D0571 8150,0775.docx, Boston Scientific, Mar. 11, 2020.

International Search Report and Written Opinion dated Aug. 16, 2022 for International Application No. PCT/US2022/027444.

\* cited by examiner

REPOSITIONABLE TISSUE-ENGAGEMENT MEMBER AND ASSOCIATED SYSTEMS AND METHODS

PRIORITY

This application claims the benefit of priority of U.S. Provisional Application No. 63/183,790, filed May 4, 2021, the entire disclosure of which is hereby incorporated by reference herein for all purposes.

FIELD

The present disclosure relates generally to the field of tissue-engagement members and associated systems and methods. More particularly, the present disclosure relates to the field of repositionable tissue-engagement members and associated systems and methods.

BACKGROUND

Physicians are becoming more proficient at endoscopic procedures using transluminally inserted tools to perform various procedures without the need for open surgery. However, with currently available technologies, conducting more complex procedures, such as endoscopic submucosal dissection (ESD) or an endoscopic mucosal resection (EMR) (which may be used to remove lesions from the gastrointestinal tract), can be difficult and time consuming. Manipulating devices for clipping tissue may require procedurally complicated and/or time-intensive techniques for positioning and orienting and re-orienting the devices and associated medical instruments. In addition, non-ideal visualization and lack of tissue tension also make the procedures difficult and time consuming. Having a means to create more significant traction force on the tissue would be desirable to improve the visualization of the cutting plane. The use of repositionable clips has become important for improving the ability to re-tension a tether losing tension as a procedure (e.g., cutting) on grasped tissue is performed. Also, repositionable clips allow for adjustment during a procedure, and facilitate device retrieval. However, current repositionable clips present challenges with respect to such factors as cost, usability, and required cognitive load for manipulation/actuation thereof.

It is with the above considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a tissue-engagement member includes a pair of jaw members coupled together and movable between a closed configuration and an open configuration. The pair of jaw members also includes an actuator operatively engaged with the pair of jaw members to shift the jaw members between the closed configuration and the open configuration. The pair of jaw members also includes a biasing element positioned to cause the jaw members to be biased into the closed configuration. The pair of jaw members also includes a cam mechanism operatively associated with at least one of the actuator, the biasing element, or at least one of the jaw members.

In some embodiments, the actuator is shiftable against the force of the biasing element to shift the jaw members from the closed configuration to the open configuration. In some embodiments, the biasing element operatively engages at least one of the actuator or at least one of the jaw members. In some embodiments, the biasing element is positioned about a portion of one of the actuator or at least one of the jaw members.

In some embodiments, the cam mechanism includes a cam surface on one of the actuator or at least one of the jaw members. In some embodiments, the cam mechanism further includes a cam follower on the other of the actuator or at least one of the jaw members. In some embodiments, the biasing element operatively engages one of the actuator or at least one of the jaw members to actuate the cam mechanism to return the jaw members to a closed configuration from an open configuration.

In some embodiments, the tissue-engagement member further includes a housing, the jaw member and the actuator positioned within a portion of the housing. In some embodiments, the biasing element operatively engages one of the actuator or the housing or at least one of the jaw members to bias the jaw members to a closed configuration.

In some embodiments, the jaw members are coupled together and biased apart from each other, the actuator is movable between a position holding the jaw members in the closed configuration and a position allowing the jaw members to move apart to the open configuration, and the biasing element biases the actuator into the position holding the jaw members in the closed configuration.

In some embodiments, the tissue-engagement member further includes an actuation element coupled to the actuator and graspable to move the actuation element to shift the jaw members between the closed and open configurations.

In accordance with various principles of the present disclosure, a tissue-engagement member includes a pair of jaw members coupled together and movable between a closed configuration and an open configuration, an actuator operatively engaged with the pair of jaw members to shift the jaw members between the closed configuration and the open configuration, and a biasing element positioned over a portion of at least one of the actuator or the jaw members to cause the jaw members to be biased into the closed configuration.

In some embodiments, the biasing element is an elastic element positioned about the jaw members.

In some embodiments, the biasing element is positioned about a portion of the actuator.

In some embodiments, the tissue-engagement member further includes a cam mechanism operatively associated with at least one of the actuator, the biasing element, or at least one of the jaw members. In some embodiments, the cam mechanism includes a cam surface on one of the actuator or at least one of the jaw members. In some embodiments, the cam mechanism further includes a cam follower on the other of the actuator or at least one of the jaw members.

In accordance with various principles of the present disclosure a tissue-engagement system includes a tissue-engagement member having a distal end and a proximal end, the tissue-engagement member including jaws along the distal end, an actuator along the proximal end, and a biasing element, where the jaws are shiftable between a closed configuration and an open configuration, the actuator is operatively engaged with the jaws to move the jaws between the closed and open configurations, and the biasing element biases the jaws into the closed configuration. The tissue-engagement system further includes a tissue-engagement-member manipulator having a distal end configured to operatively engage with the tissue-engagement member to move the actuator to shift the jaws between the closed and open configurations, and a manipulator deployment system configured to deliver and to maneuver the tissue-engagement-member manipulator to move the actuator.

In some embodiments, an actuation element is operatively coupled with a proximal end of the actuator along the proximal end of the tissue-engagement member; and an actuator-engagement element is provided on a distal end of the tissue-engagement-member manipulator and configured to engage with the actuation element in a range of orientations with respect to the actuation element.

In some embodiments, the manipulator deployment system further includes a flexible tubular element with a lumen defined therethrough, and a sheath, where the tissue-engagement-member manipulator is movable proximally into the lumen defined through the flexible tubular element to bring the proximal end of the tissue-engagement member into abutment with a distal end of the flexible tubular element, and the sheath is movable over the distal end of the flexible tubular element and over the tissue-engagement member to hold the tissue-engagement member in alignment with the manipulator deployment system.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

4

Figure 1:
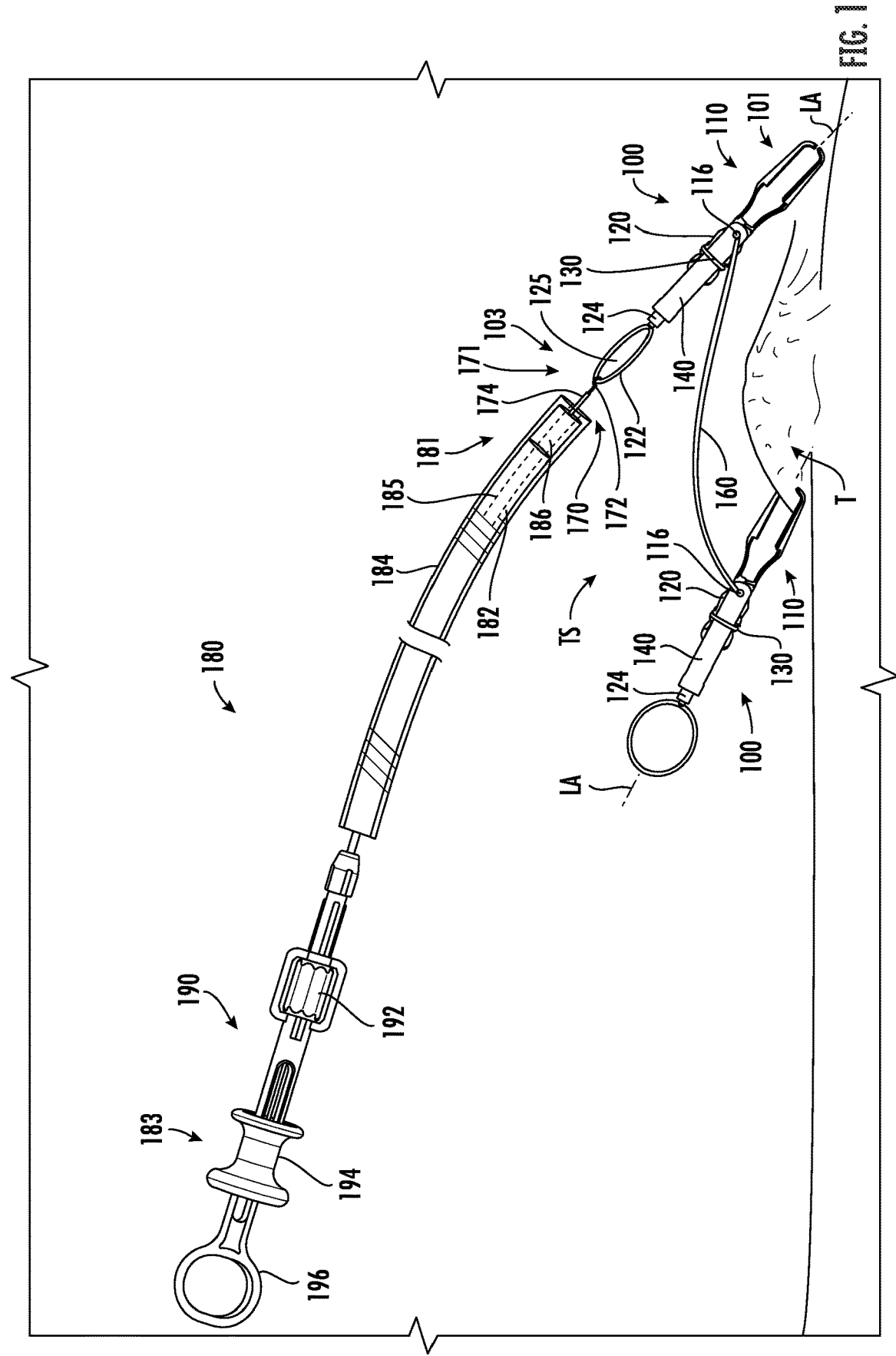
FIG. 1 illustrates a perspective view of an example of an embodiment of a tissue-engagement member and associated system in accordance with various aspects of the present disclosure.
Figure 2:
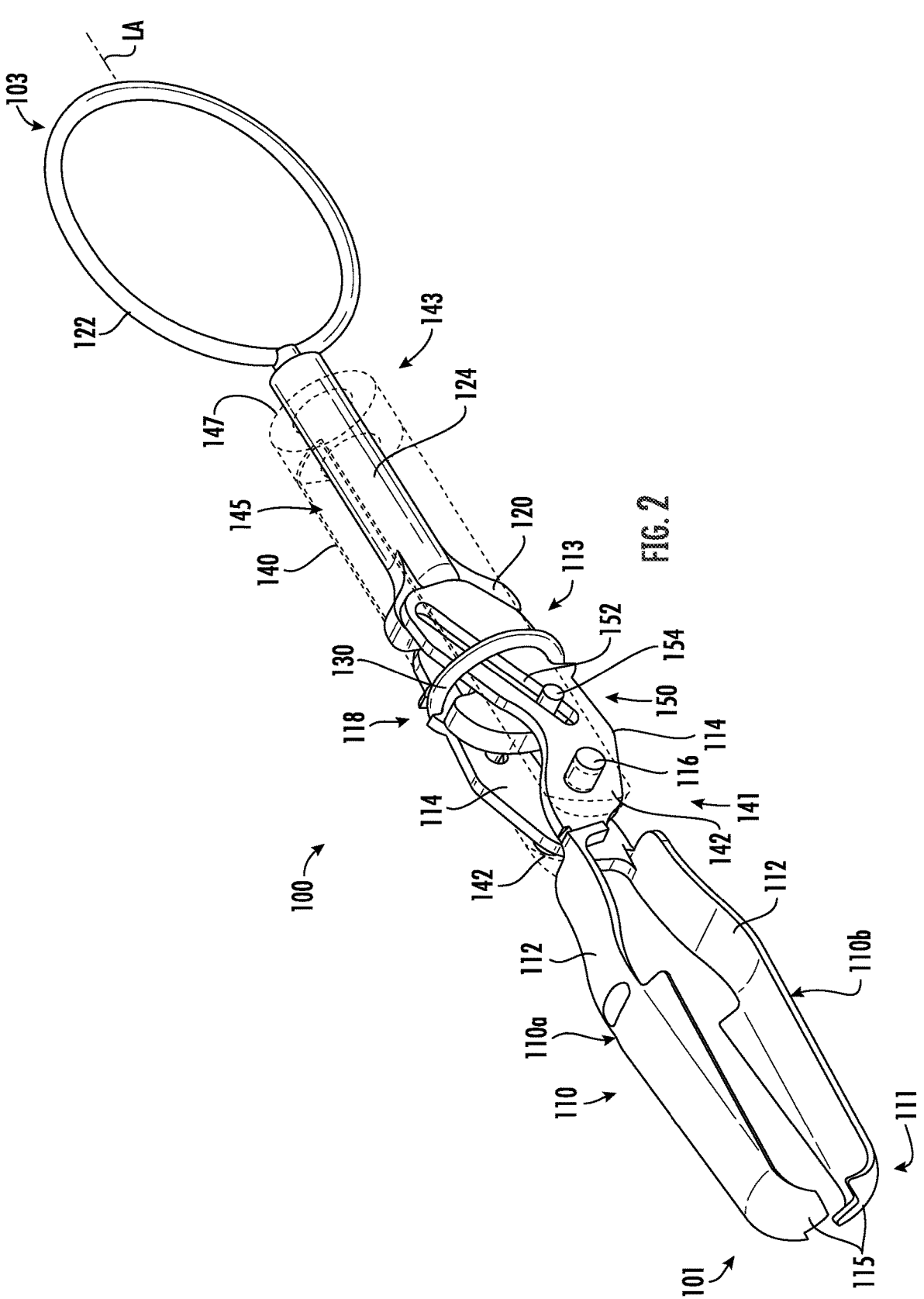

FIG. 2 illustrates a perspective view of a tissue-engagement member as in FIG. 1.

Figure 3:
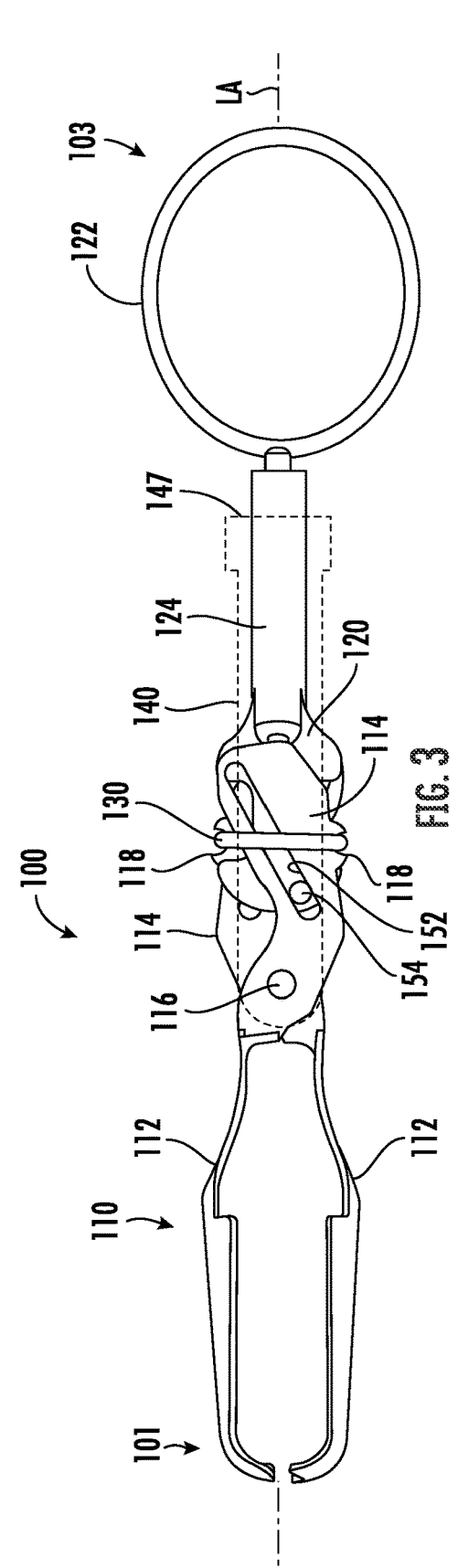

FIG. 3 illustrates an elevational view of a tissue-engagement member as in FIG. 2 with an outer portion in phantom to reveal internal components, and showing the tissue grasping portions in a closed configuration.

Figure 4:
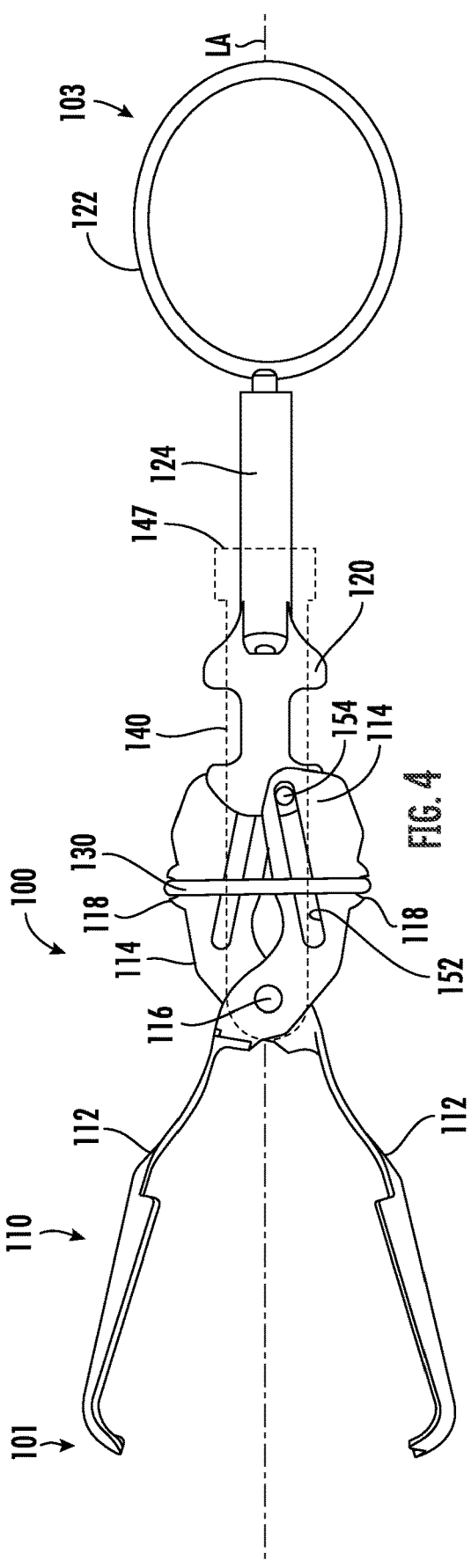

FIG. 4 illustrates an elevational view of a tissue-engagement member as in FIG. 2 and FIG. 3 with an outer portion in phantom to reveal internal components, and showing the tissue grasping portions in an open configuration.

Figure 5:
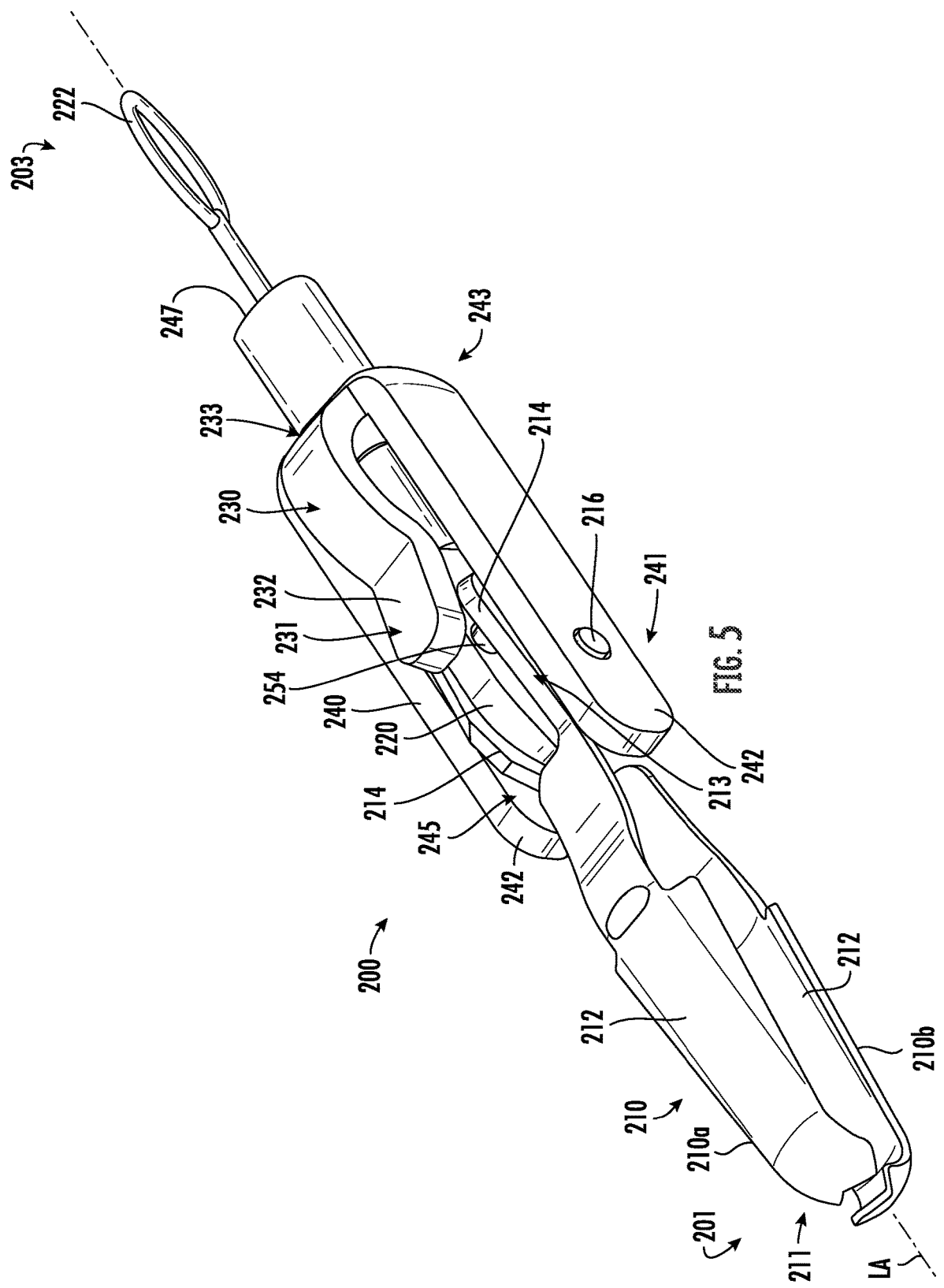

FIG. 5 illustrates a perspective view of another embodiment of a tissue-engagement member which may be used with a system as illustrated in FIG. 1.

Figures 6, 7:
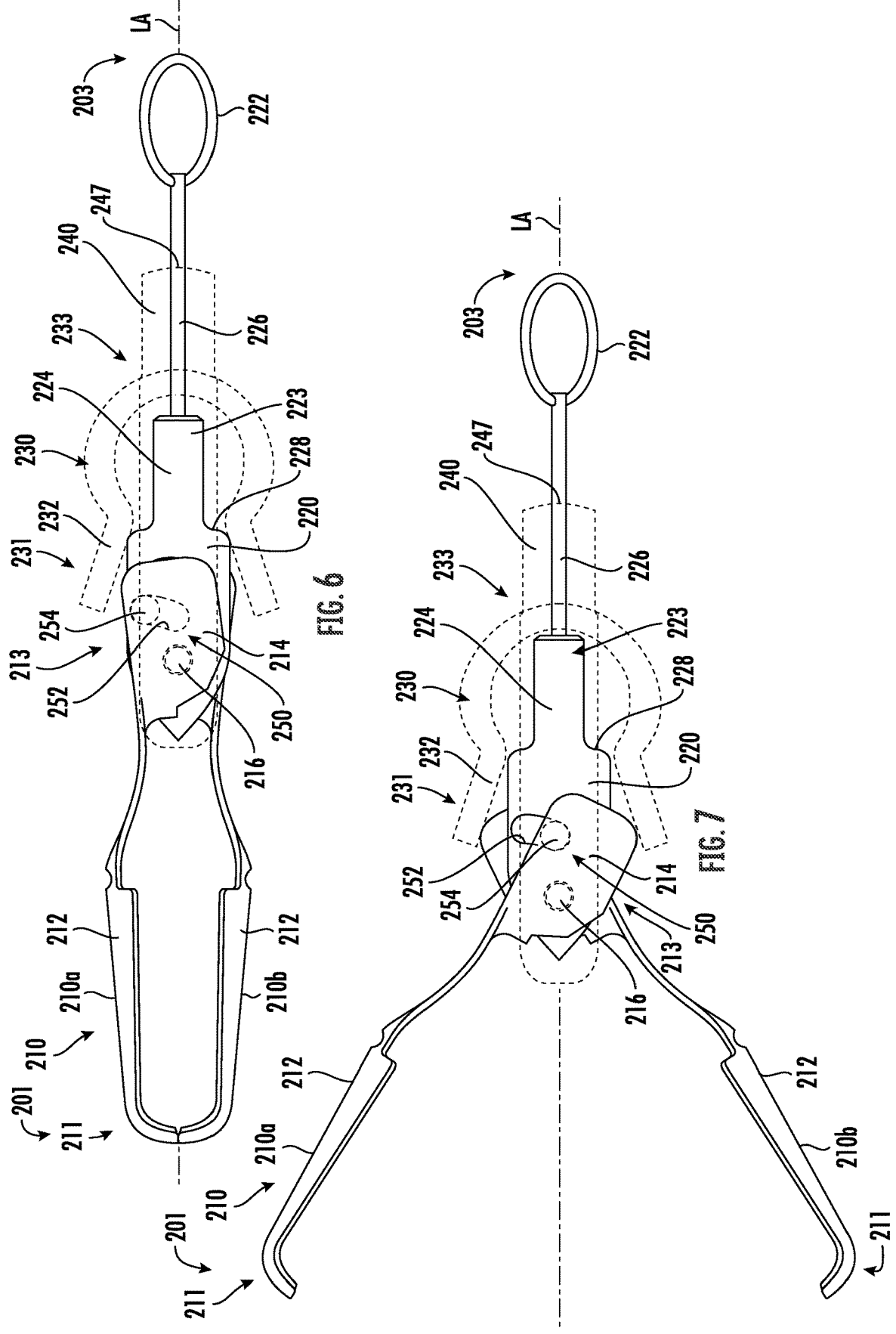

FIG. 6 illustrates an elevational view of a tissue-engagement member as in FIG. 5 with an outer portion in phantom to reveal internal components, and showing the tissue grasping portions in a closed configuration.

FIG. 7 illustrates an elevational view of a tissue-engagement member as in FIG. 5 and FIG. 6 with an outer portion in phantom to reveal internal components, and showing the tissue grasping portions in an open configuration.

Figure 8:
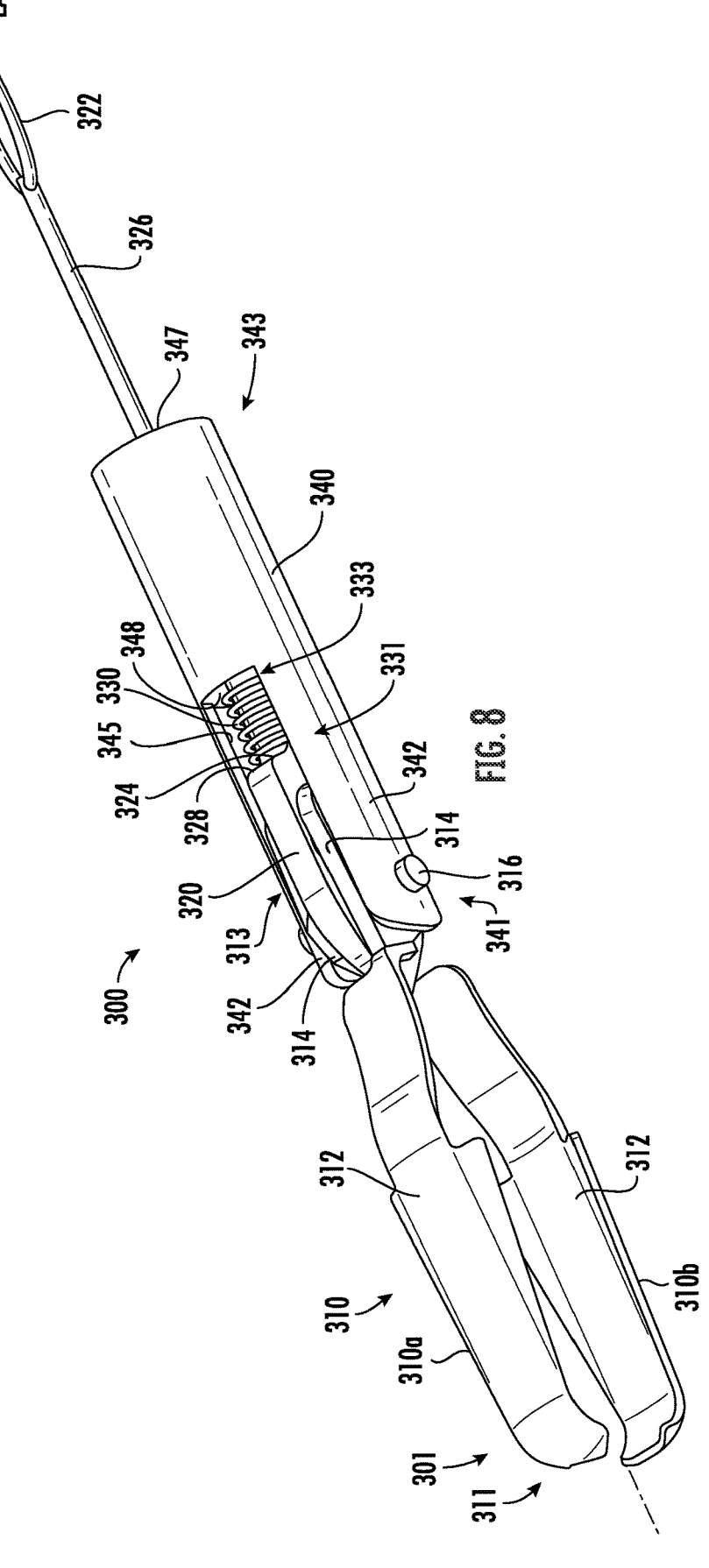

FIG. 8 illustrates a perspective view of another embodiment of a tissue-engagement member which may be used with a system as illustrated in FIG. 1.

Figures 9, 10:
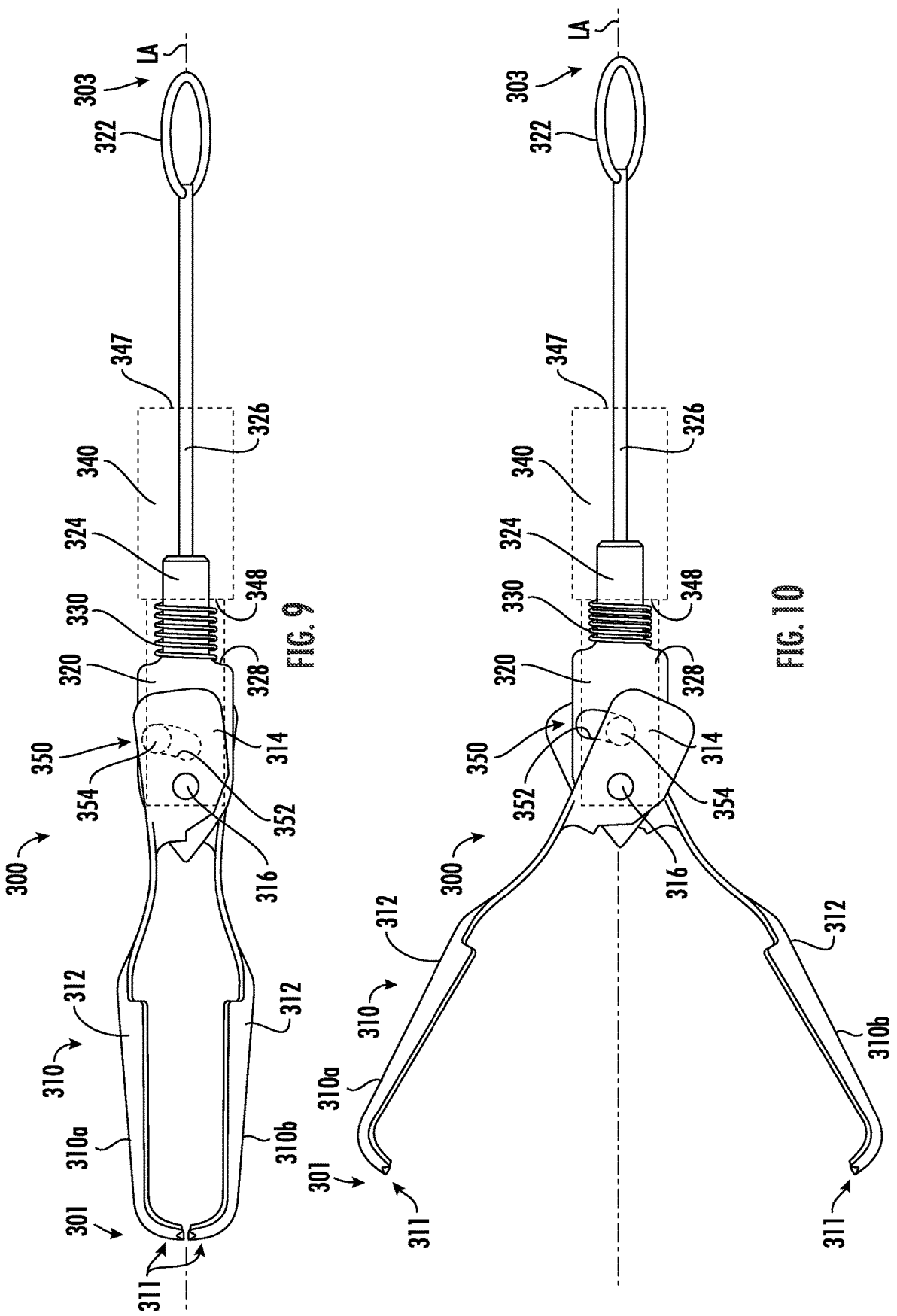

FIG. 9 illustrates an elevational view of a tissue-engagement member as in FIG. 8 with an outer portion in phantom to reveal internal components, and showing the tissue grasping portions in a closed configuration.

FIG. 10 illustrates an elevational view of a tissue-engagement member as in FIG. 8 and FIG. 9 with an outer portion in phantom to reveal internal components, and showing the tissue grasping portions in an open configuration.

Figure 11:
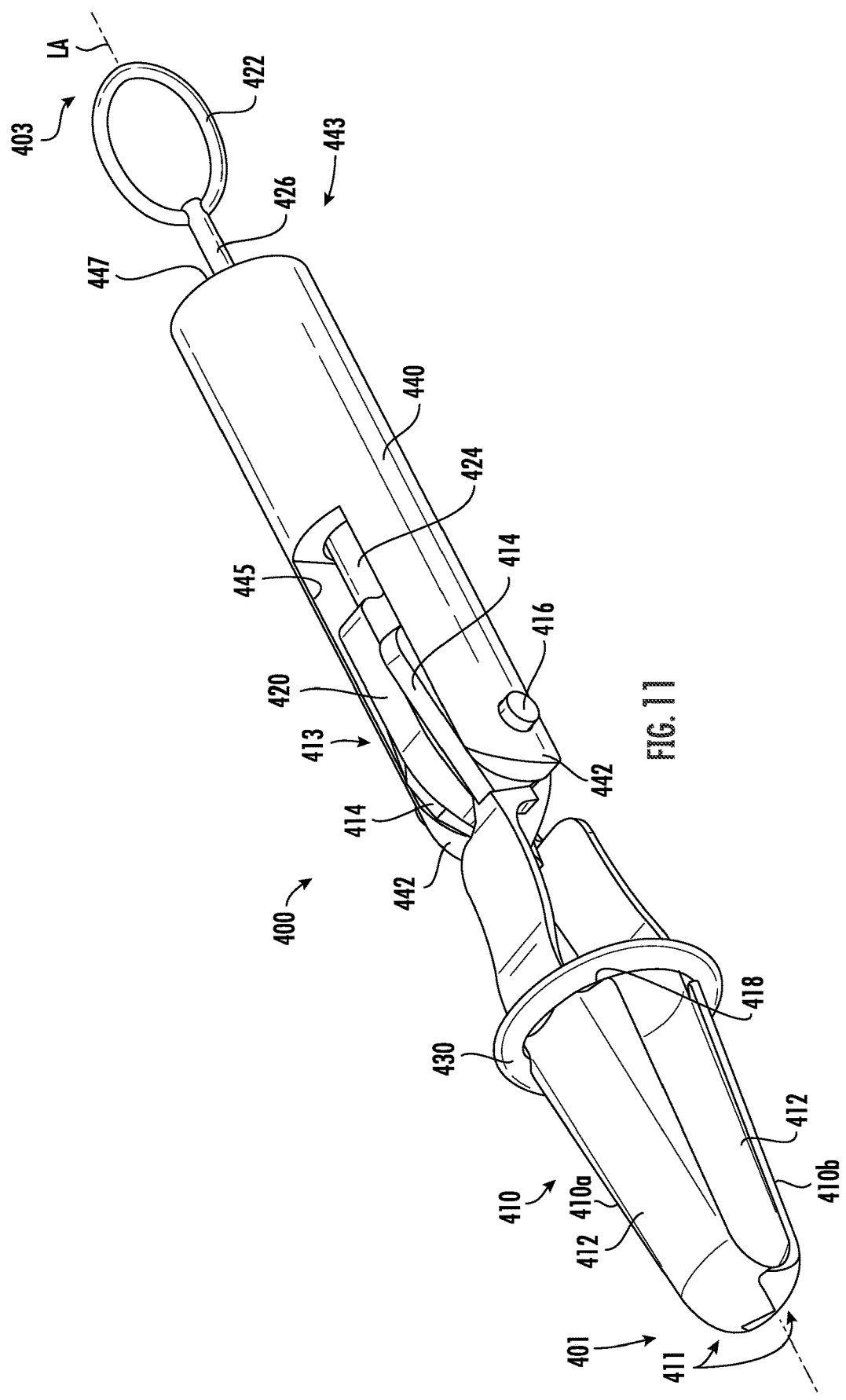

FIG. 11 illustrates a perspective view of another embodiment of a tissue-engagement member which may be used with a system as illustrated in FIG. 1.

Figures 12, 13:
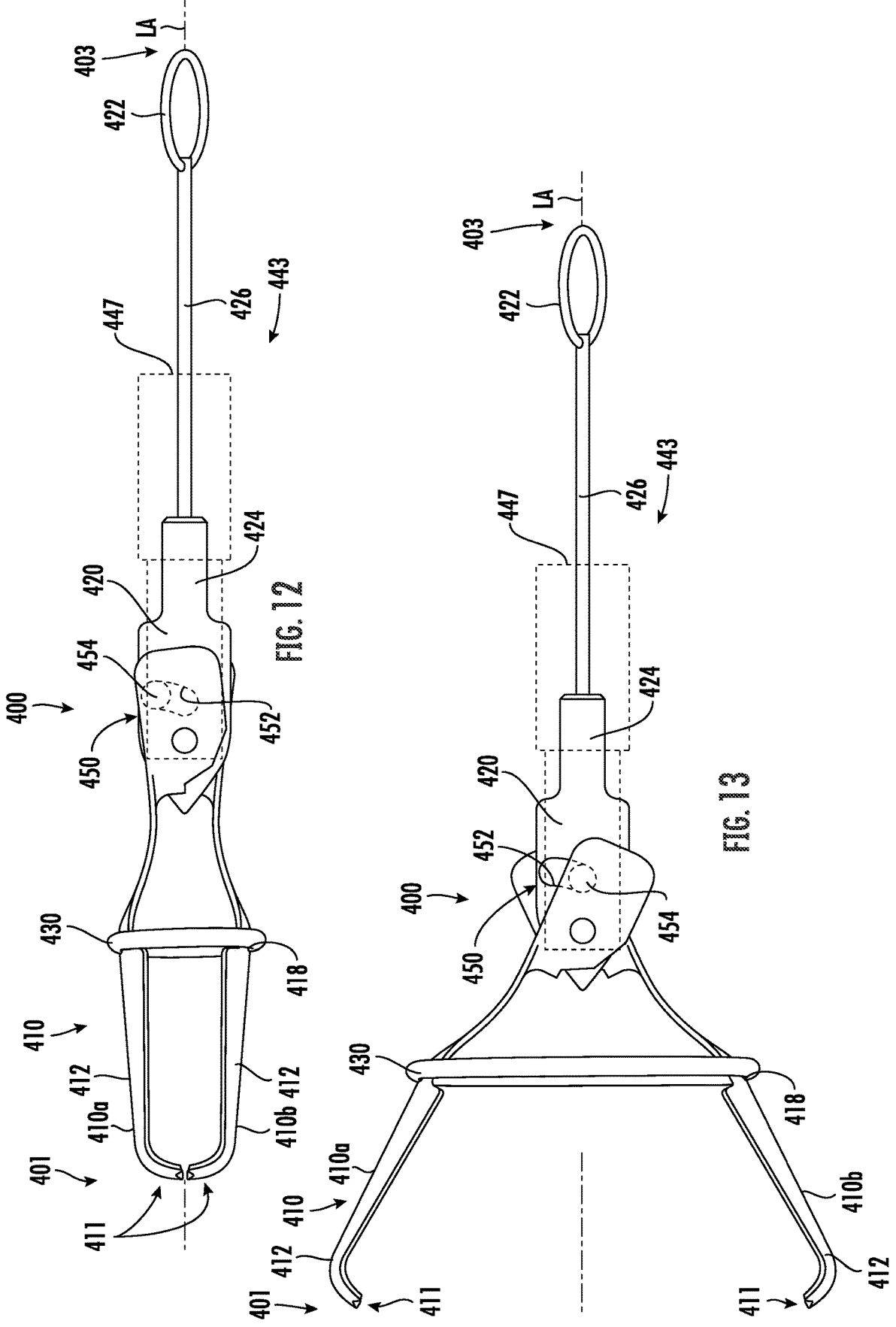

FIG. 12 illustrates an elevational view of a tissue-engagement member as in FIG. 11 with an outer portion in phantom to reveal internal components, and showing the tissue grasping portions in a closed configuration.

FIG. 13 illustrates a perspective view of a tissue-engagement member as in FIG. 11 and FIG. 12 with an outer portion in phantom to reveal internal components, and showing the tissue grasping portions in a closed configuration.

Figure 14:
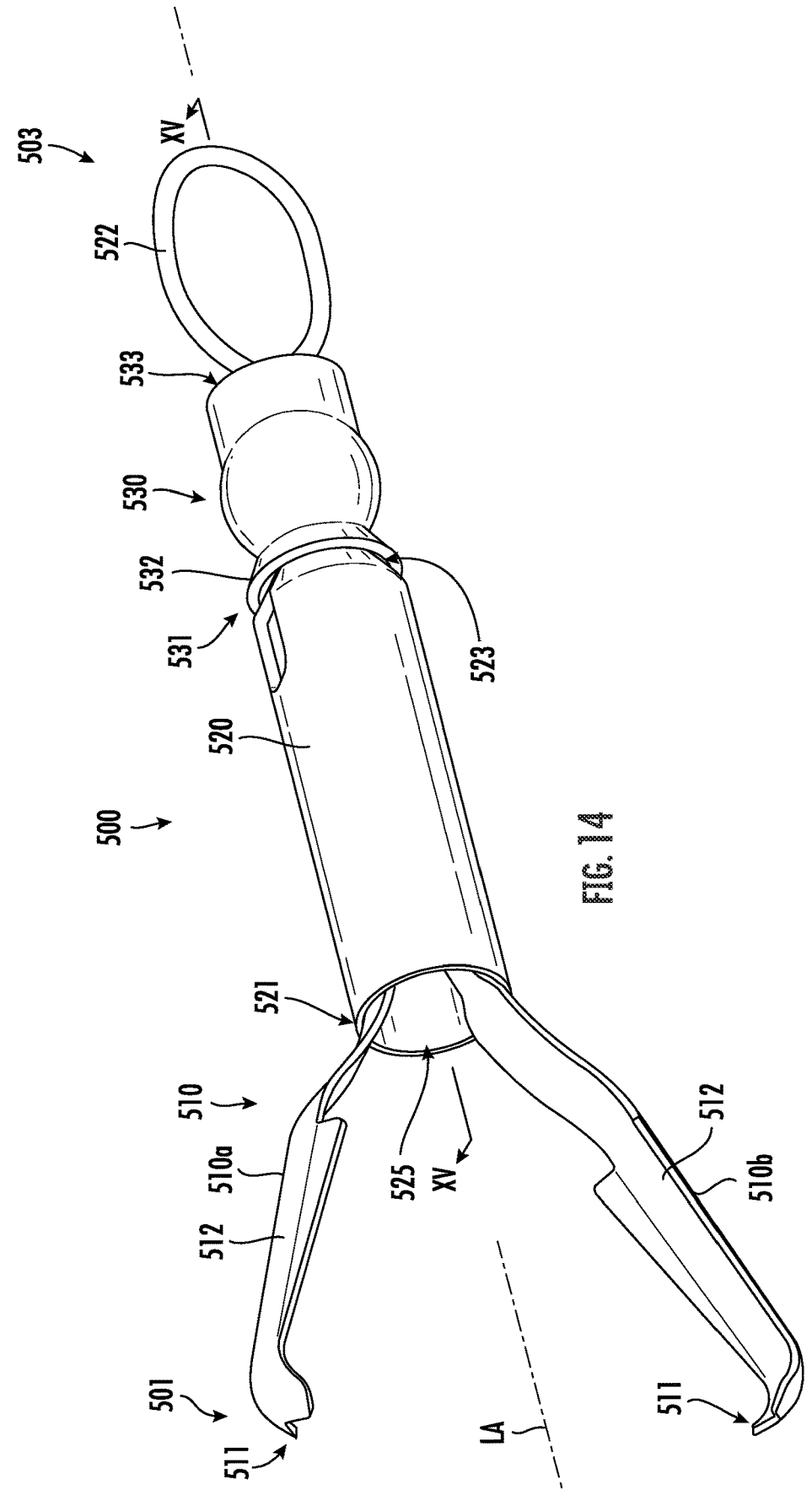

FIG. 14 illustrates a perspective view of another embodiment of a tissue-engagement member which may be used with a system as illustrated in FIG. 1.

Figure 15:
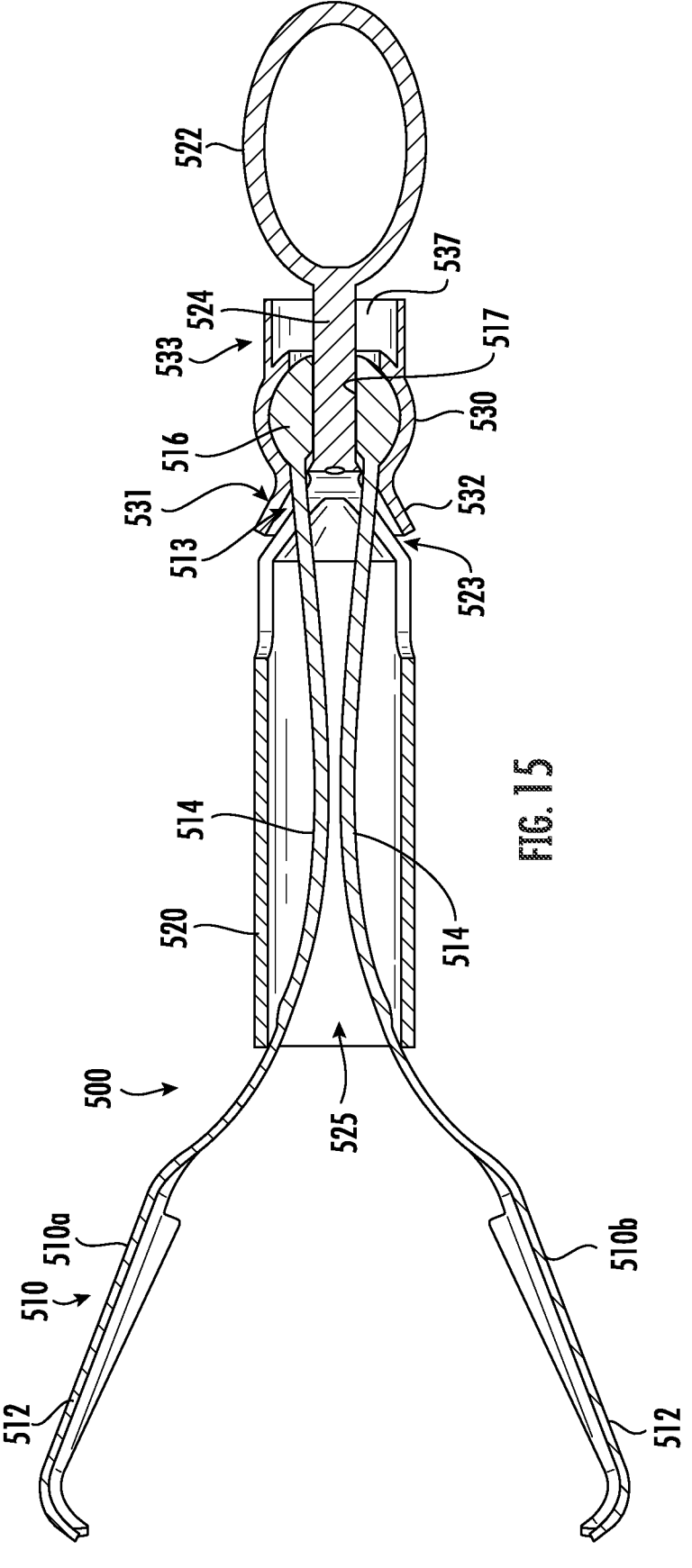

FIG. 15 illustrates a cross-sectional view along line XV-XV of FIG. 14 of an embodiment of a tissue-engagement member as in FIG. 14.

Figures 16, 17:
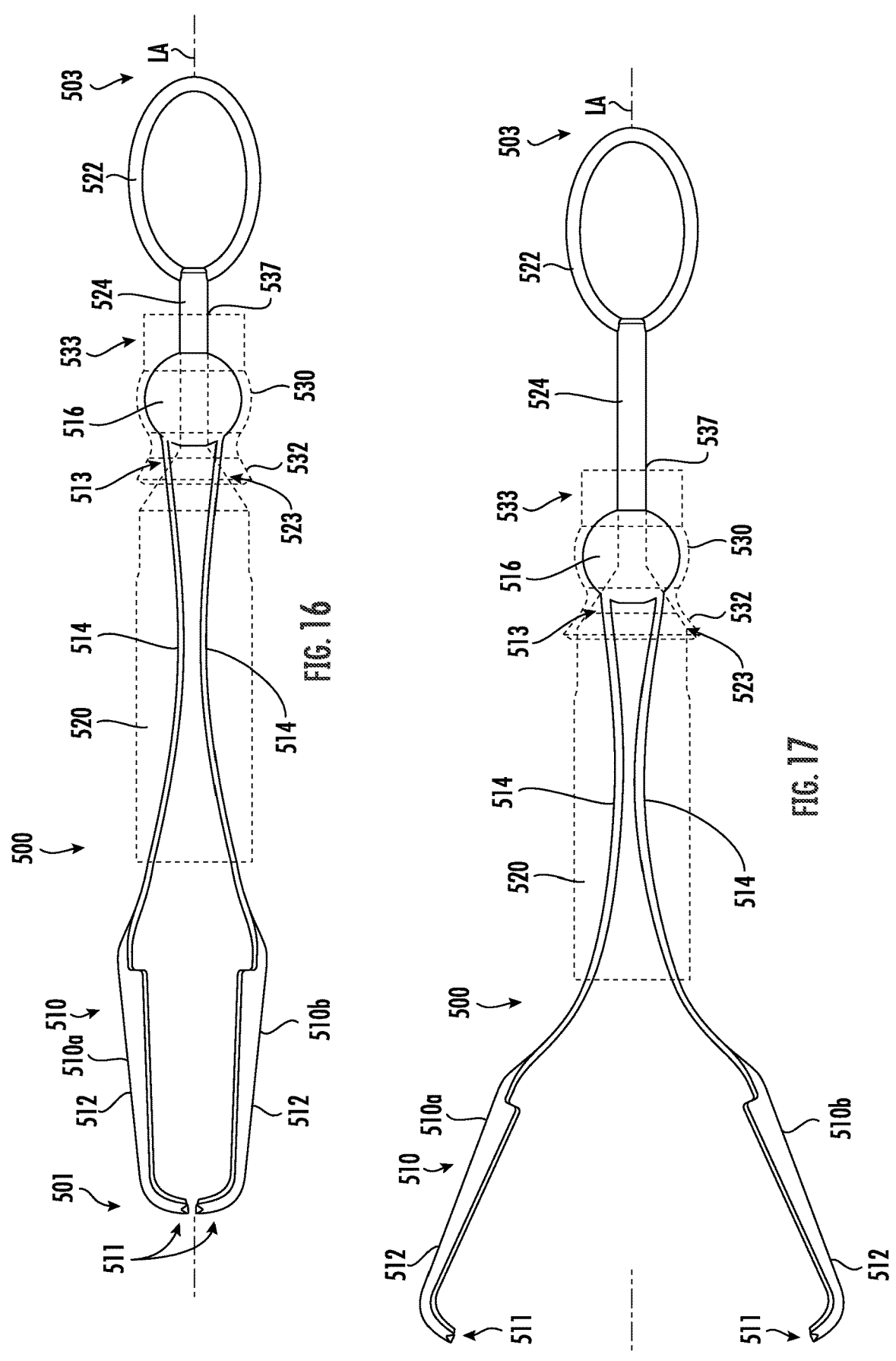

FIG. 16 illustrates a perspective view of a tissue-engagement member as in FIG. 14 and FIG. 15 with an outer portion in phantom to reveal internal components, and showing the tissue grasping portions in a closed configuration.

FIG. 17 illustrates a perspective view of a tissue-engagement member as in FIGS. 14-16 with an outer portion in phantom to reveal internal components, and showing the tissue grasping portions in an open configuration.

Figure 18:
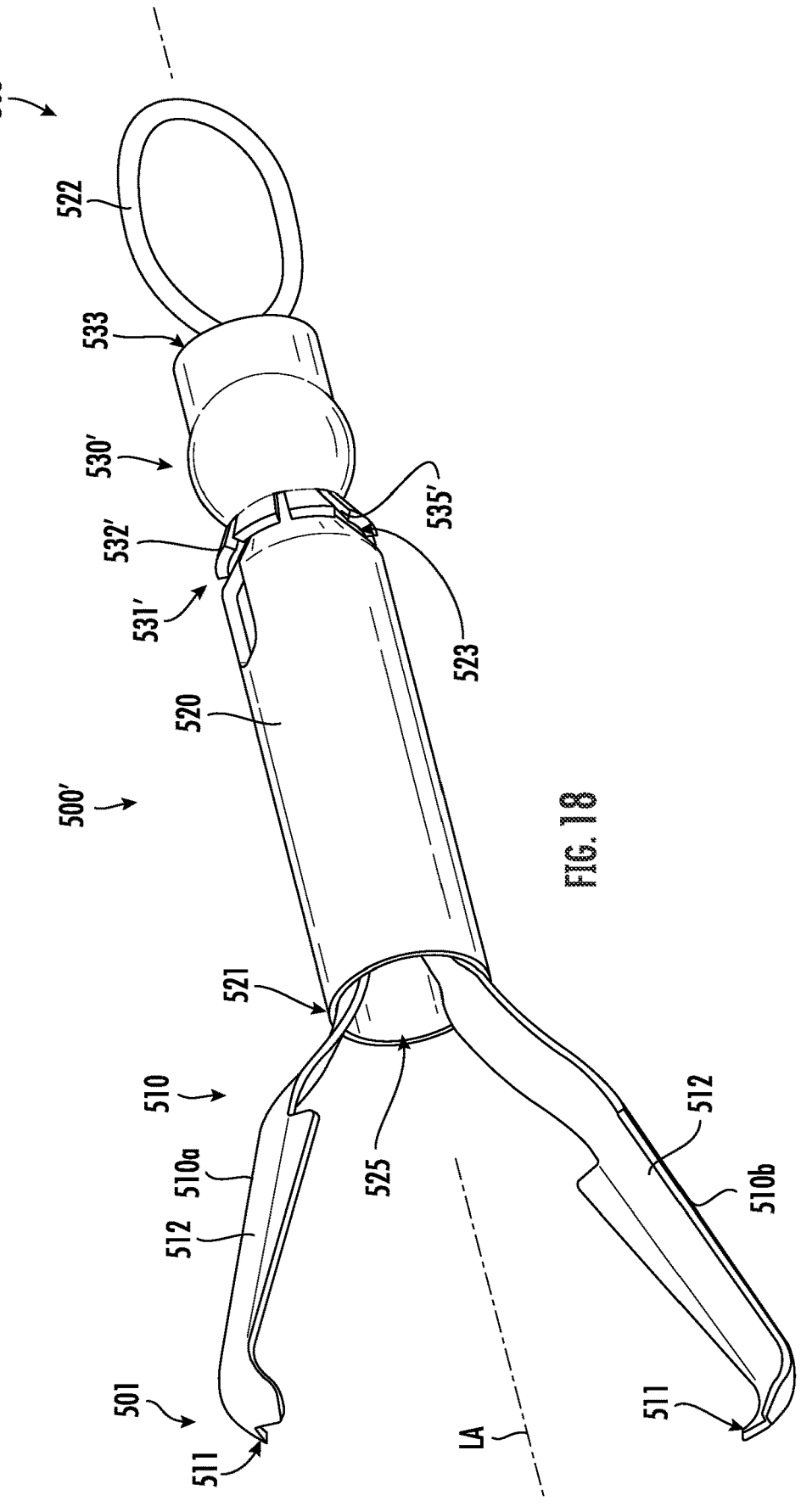

FIG. 18 illustrates a perspective view of a variation of a tissue-engagement member as in FIGS. 14-17 and which may be used with a system as illustrated in FIG. 1.

Figures 19, 20, 21:
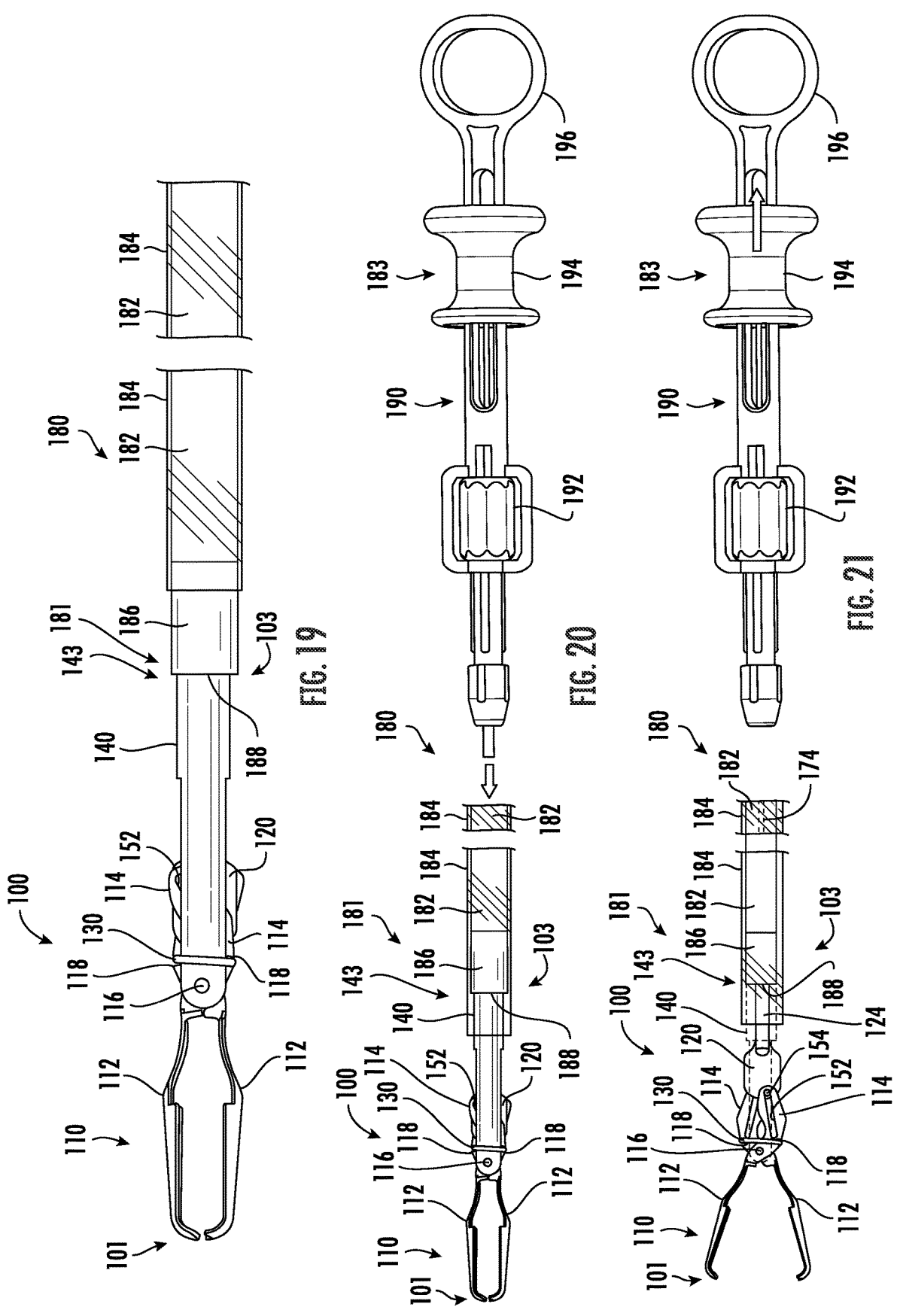

FIG. 19-21 illustrate sequential positions of a tissue-engagement member and a tissue-engagement-member manipulator from a closed configuration of the tissue-engagement member to an open configuration of the tissue-engagement member.

DETAILED DESCRIPTION

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a channel, a cavity, or a bore.

In accordance with various principles of the present disclosure, a tissue-engagement member has a first tissue-engaging element and a second tissue-engaging element movably coupled with respect to each other to engage, contact, grip, grasp, etc., with body tissue. For the sake of convenience, and without intent to limit, reference will be made to a jaw rather than a tissue-engaging element. The jaws of a tissue-engagement member formed in accordance with various principles of the present disclosure may include a pair of jaw members which are movable with respect to each other between a closed configuration, in which the jaw members are in contact with each other or are substantially in contact (e.g., with tissue grasped therebetween) with each other, and an open configuration in which the jaw member are spaced apart (e.g., to allow tissue to be positioned therebetween or to be removed or released from between the jaw members). It will be appreciated that a tissue-engagement member formed in accordance with various principles of the present disclosure may also be referenced as a clip, clasp, fastener, clamp, etc., without intent to limit. Reference may be made herein simply to the jaws, rather than the jaw members, for the sake of simplicity and without intent to limit.

In accordance with various principles of the present disclosure, a biasing element is provided to maintain the jaws of a tissue-engagement member in a closed configuration. In some embodiments, the jaws are in a closed configuration when the biasing element in a rest position. It will be appreciated that terms such as rest, neutral, unbiased, undeformed, etc., may be used interchangeably herein to indicate a state with no built up or stored potential energy. It will further be appreciated that terms such as configuration and position (and conjugations and other grammatical forms thereof) may be used interchangeably herein without intent to limit. The biasing element may be formed as a separate element (e.g., separately from the jaws of the tissue-engagement member). The biasing element may be in the form of an elastic band or a spring-biased metal element.

In embodiments in which the biasing element maintains the jaws in a closed configuration when the biasing element is in a rest position, the biasing element must be shifted into another configuration or position, such as a potential-energy-storing configuration, to allow the jaws to shift to an open configuration. In some embodiments, an actuator may be provided to move the jaws into an open configuration, such as by moving the biasing element into a potential-energy-storing configuration. In some embodiments, the actuator moves the jaws against the force of the biasing element. In some embodiments, the actuator moves against the force of the biasing element.

In some embodiments, the jaws of the tissue-engagement member are pivotably coupled together and a biasing element maintains the jaws in a closed configuration. An actuator may be provided in such embodiments to move the jaws against the biasing force of the biasing element into an open configuration and to hold jaws in the open configuration. When the actuator is released, the biasing element may be positioned and/or configured to return the jaws to the closed configuration.

In some embodiments, a cam mechanism is associated with at least one of the actuator, the biasing element, or at least one of the jaw members. The cam mechanism may include a cam surface and a cam follower. In some embodiments, a cam surface is provided on one of either the actuator or a jaw member (one or both of the jaw members), and a cam follower is provided on the other of the actuator or a jaw member (one or both of the jaw members). Movement of the actuator with respect to the jaw members causes the cam follower to move along the cam surface to cause the jaw members to move between the closed configuration and the open configuration.

In some embodiments, the jaws are biased into an open configuration, and the biasing element maintains the jaws in a closed configuration. For instance, the biasing element may bias an actuator into a jaw-closing position to hold the jaws of the tissue-engagement member in the closed configuration. In some embodiments, an actuator is positionable over the jaws to hold the jaws in a closed configuration. The actuator may be shifted to allow the jaws to shift to an open configuration, such as by being shifted against the biasing element. When the actuator is released, the biasing element may be positioned and/or configured to return the actuator back to the jaw-closing position to shift the jaws back to the closed configuration.

In some embodiments, the biasing element is provided over a portion of the tissue-engagement member. In some embodiments, the biasing element contacts an outer surface of the tissue-engagement member. In some embodiments, the biasing element contacts the jaws of the tissue-engagement member. In some embodiments, an actuator is operatively associated with the jaws to cause the jaws to move between the closed and open configurations, and the biasing element contacts the actuator. In some embodiments, the biasing element surrounds a portion of the tissue-engagement member. In some embodiments, the biasing element surrounds the jaws of the tissue-engagement member. In some embodiments, an actuator is operatively associated with the jaws to cause the jaws to move between the closed and open configurations, and the biasing element surrounds the actuator. In some embodiments, the biasing element contacts and/or surrounds at least one of the jaws or an actuator of the tissue-engagement member.

As noted above, in some embodiments an actuator is provided to shift the jaws between the closed configuration and the open configuration. The actuator may be coupled or linked with the jaws to move the jaws between the open and closed configurations, or may operatively engage the jaws without being linked with the jaws. The actuator may be positioned with respect to the jaws such that linear movement of the actuator causes the jaws to shift between a closed configuration and an open configuration.

An actuation element may be provided and arranged and configured to facilitate operative engagement of the actuator to cause the tissue-engagement member to shift between open and closed configurations. The actuation element may be an actuator-engagement element configured to facilitate operative engagement with the actuator. However, other configurations of actuation elements are within the scope and spirit of the present disclosure. Reference may be made herein to provided, associated, coupled, engaged, etc. to describe physical relationships of the actuation element with at least one part or component of the tissue-engagement member, such terms being used interchangeably herein without intent to limit unless otherwise indicated. The actuation element is configured to be operatively engaged by an instrument with an actuator-engaging element. It will be appreciated that terms such as associated, coupled, engaged, contacted, connected, linked, etc. (including conjugations and other grammatical forms thereof) may be used interchangeably herein without intent to limit unless otherwise indicated. In some embodiments, the actuation element is configured to facilitate operative engagement with an actuator-engaging element without regard to the orientation of the tissue-engagement member with respect to tissue being grasped by the jaws of the tissue-engagement member. In some embodiments, the actuator-engaging element may operatively engage the actuation element in more than one orientation with respect to the actuation element. In some embodiments, the actuation element is configured to facilitate operative engagement with the actuator-engaging element when the actuator-engaging element is positioned within a range of angular positions with respect to the actuation element. For instance, the actuation element may be configured to allow operative engagement with the actuator-engaging element when the actuator-engaging element is positioned up to about 90° from an aligned (e.g., ideally aligned) position with respect to the actuation element. In accordance with various principles of the present disclosure, a tissue-engagement-member manipulator is provided with an actuator-engaging element configured to operatively engage the actuation element.

In accordance with various principles of the present disclosure, one or more tissue-engagement members are provided in a tissue-engagement system. The system may also include a tissue-engagement-member manipulator configured to actuate at least one of the tissue-engagement members to shift the jaws of the tissue-engagement member between closed and open configurations. The tissue-engagement-member manipulator may be pre-loaded in operative engagement with a tissue-engagement member to facilitate quick deployment of the tissue-engagement member. The system may further include a deployment system configured to deliver and maneuver the a tissue-engagement-member manipulator to deploy and/or maneuver a tissue-engagement member.

Various embodiments of tissue-engagement members will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

It will be appreciated that in the following description, elements or components similar among the various illustrated embodiments are generally designated with the same reference numbers increased by 100 and redundant description is omitted. Description of similar elements with similar descriptions may be omitted for the sake of brevity, reference being made to description of one element as applicable to another similar element. Common features are identified by common reference elements and, for the sake of brevity, the descriptions of the common features are generally not repeated. For purposes of clarity, not all components having the same reference number are numbered.

Turning now to the drawings, an example of an embodiment of a tissue-engagement member 100 formed in accordance with various principles of the present disclosure is illustrated grasping tissue T. Another example of an embodiment of a tissue-engagement member 100 formed in accordance with various principles of the present disclosure is illustrated in FIG. 1 being operatively engaged by a tissue-engagement-member manipulator 170. The tissue-engagement member 100 in the illustration of FIG. 1 may be used to impart traction to tissue with the use of a tether 160 extending between (and joining) the tissue-engagement members 100 in a manner known or heretofore known. The tether 160 may be traction band, elastic band, stretchable elongate member, wire, cord, cable, spring, suture, and/or any other suitable elongate member, which optionally is stretchable or elongatable. It will be appreciated that other uses of a tissue-engagement member formed in accordance with various principles of the present disclosure are within the scope and spirit of the present disclosure. Moreover, it will be appreciated that although FIG. 1 illustrates one of the embodiments of a tissue-engagement member 100 disclosed herein, any of the other tissue-engagement member 200, 300, 400, 500, 500' may be illustrated in a similar environment for use and manipulation in a similar manner.

The tissue-engagement member 100 illustrated in FIG. 1 has tissue-engaging jaws 110 along a distal end 101 of the tissue-engagement member 100. The jaws 110 are moveable between a closed configuration (as shown in FIG. 3, and as illustrated in FIG. 1 with tissue T grasped between the jaws 110) and an open configuration (as shown in FIG. 4). An actuator 120 (shown in greater detail in FIGS. 2-4) is operatively associated with the jaws 110 to cause the jaws 110 to move between the open and closed configurations. In the illustrated embodiment, a biasing element 130 maintains the jaws 110 in the closed configuration. The biasing element 130 may be in the form of a rubber band, o-ring, or other elastic element capable of being positioned in operative association with, such as around, the jaws 110. A casing or housing 140 (hereinafter housing, for the sake of convenience and without intent to limit), such as in the form of a clevis, may be positioned about the jaws 110 and actuator 120. In the illustrated embodiment, the biasing element 130 extends about the housing 140. The housing 140 may be formed by a relatively simple stamping process, facilitating and lowering the manufacturing cost of the tissue-engagement member 100.

In accordance with various principles of the present disclosure, an actuation element 122 is operatively associated with a proximal end 103 of the tissue-engagement member 100 to facilitate actuation of the tissue-engagement member 100 to shift between the closed and open configurations. In the illustrated embodiment, the actuation element 122 is in the form of a loop which may readily be engaged by an actuator-engaging element 172 of a tissue-engagement-member manipulator 170, as discussed in further detail below. However, other configurations of an actuation element 122 permitting ready engagement thereof are within the scope and spirit of the present disclosure. In accordance with various principles of the present disclosure, the actuation element 122 may be moved longitudinally along the longitudinal axis LA of the tissue-engagement member 100 to actuate the actuator 120 to shift the jaws 110 between the open and closed configurations. The manner in which the tissue-engagement member 100 operates and the mechanism by which the actuator 120 and jaws 110 interact in the example of an embodiment of a tissue-engagement member 100 illustrated in FIG. 1 will be better appreciated with reference to FIGS. 2-4.

A perspective view of an example of an embodiment of a tissue-engagement member 100 is illustrated in FIG. 2 with its housing 140 in phantom to reveal the arrangement of elements of the tissue-engagement member 100 resulting in the desired operational characteristics of the tissue-engagement member 100.

The jaws 110 of the tissue-engagement member 100 include a pair of jaw members 110a, 110b each having a tissue-engaging end 112 (functionally, the ends between which an element, such as tissue, is to be grasped) along a distal end 111 of the jaws 110. The tissue-engaging distal ends 111 of the jaws 110 are illustrated as having interengaging teeth 115, although other configurations are within the scope and spirit of the present disclosure. A shank 114 (which may be referenced as a shaft or wing without intent to limit) extends proximally from each tissue-engaging end 112 along the proximal end 113 of the jaw members 110a, 110b. As may be seen through the phantom depiction of the housing 140, the shanks 114 of the jaws 110 extend between the prongs or legs or arms 142 (hereinafter arms, for the sake of convenience and without intent to limit) of the generally clevis-shaped housing 140. The jaw members 110a, 110b of the jaws 110 are pivotable about a pivot pin 116 to pivot with respect to each other between closed and open configurations. The pivot pin 116 may be mounted with respect to the distal end 141 of the housing 140 to maintain the jaws 110 mounted with respect to the housing 140. It will be appreciated that the pivot pin 116 may extend through both jaw members 110a, 110b, or each jaw member 110a, 110b may have a respective outwardly extending pivot pin 116 facing towards and mounted with respect to an arm 142 of the housing 140. It is noted that a tether 160 may be coupled to the tissue-engagement member 100 such as via the pivot pin 116, as illustrated in the embodiment of FIG. 1, and optionally via a hinge or other extension coupled to or formed with the pivot pin 116. Other configurations, such as coupling via the housing 140, are within the scope and spirit of the present disclosure.

The actuator 120 is operatively associated with the jaws 110 to effect shifting of the jaws 110 between the closed and open configurations as will be described in further detail below, such as with reference to FIG. 3 and FIG. 4. The actuator 120 is positioned adjacent the shanks 114 of the jaws 110 and between the arms 142 of the housing 140. The actuator 120 may be larger in at least one dimension than the diameter of the housing 140 and thus may extend through a window 145 provided in the housing 140 to allow proximal sliding of the actuator 120 to actuate the jaws 110.

A cam mechanism 150 is operatively associated with the actuator 120 and the jaws 110 of the tissue-engagement member 100. As may be seen through the phantom lines of the housing 140, the cam mechanism 150 of the example of an embodiment of a tissue-engagement member 100 illustrated in FIG. 2 associates the actuator 120 with the proximal end 113 of the jaws 110 generally within the window 145 of the housing 140 between the housing arms 142. The cam mechanism 150 is configured and arranged so that movement of the actuator 120 shifts the jaws 110 between the closed configuration illustrated in FIG. 3 and the open configuration illustrated in FIG. 4. More particularly, the cam mechanism 150 includes a cam surface 152 and a cam follower 154 which moves along cam surface 152. It will be appreciated that various terms may be used interchangeably herein to describe the motion of the cam follower 154, such as ride, slide, extend, translate, shift, etc., without intent to limit. In the illustrated embodiment, the cam surface 152 is in the form of slots in the respective shanks 114 along the respective proximal ends 113 of the jaw members 110a, 110b, and the cam follower 154 is in the form of a pin extending from either side of the actuator 120 facing a jaw member 110a, 110b to slide within a respective slot. It will be appreciated that a reverse configuration (with inwardly-facing, actuator-facing pins on the shanks 114 and respective slots for the pins on outwardly-facing, shank-facing sides of the actuator 120) or other configurations of cam mechanism 150 are within the scope and spirit of the present disclosure.

Operation of the cam mechanism 150 may be more readily appreciated with reference to FIG. 3 and FIG. 4. A biasing element 130 is operatively associated with the jaws 110 and interacts with the jaws 110 to hold the jaws 110 in a closed configuration with the cam mechanism 150 in a closed configuration, as illustrated in FIG. 3. In the illustrated embodiment, the biasing element 130 is positioned about the shanks 114 of the jaws 110 along the proximal end 103 of the jaws 110 to encircle or surround the shanks 114, and the biasing element 130 operatively engages the jaws 110. However, other positions and configurations of a biasing element 130 are within the scope and spirit of the present disclosure. As described above, the tissue-engagement member 100 includes an actuation element 122 arranged and configured to affect the actuator 120 (by moving or shifting the actuator 120 with respect to the jaws 110 and/or the cam mechanism 150) to effect shifting of the jaws 110 between closed and open configuration. Longitudinal shifting, along the longitudinal axis LA of the tissue-engagement member 100 as well as generally longitudinally along a deployment system 180 (as in FIG. 1), is considered one of the simpler motions to effect within a body, such as transluminally.

In the embodiment of a tissue-engagement member 100 illustrated in FIGS. 2-4, the actuation element 122 is coupled to the actuator 120 via a shaft 124. The shaft 124 extends proximally toward the proximal end 103 of the tissue-engagement member 100 from the actuator 120 through an axial opening 147 at the proximal end 143 of the housing 140 to be coupled with the actuation element 122. The coupling of the actuation element 122 may be accomplished in any known or heretofore manner such as brazing or welding (e.g., of metal materials) mechanical deformation and coupling (such as crimping) or co-molding (of polymeric materials) or other coupling. In some embodiments, at least the actuation element 122 and the shaft 124 are formed as a unitary, single piece (e.g., the actuation element 122 is bent from or co-molded with the element forming the shaft 124). In other embodiments, such as described below, an actuation element and shaft are formed as separate elements coupled together in any desired manner known or heretofore known in the art. Proximal retraction of the actuation element 122 (in a direction towards proximal end 103 and away from distal end 101 of the tissue-engagement member 100, such as may be appreciated upon comparison of movement from the position illustrated in FIG. 2 to the position illustrated in FIG. 3) causes proximal movement of shaft 124 and consequent proximal movement of the actuator 120. As the actuator 120 moves proximally, the cam followers 154 extending therefrom ride along the cam surfaces 152 provided on the shanks 114 of the jaws 110, such as from a position as illustrated in FIG. 2 to a position as illustrated in FIG. 3. As the cam followers 154 ride along the cam surfaces 152, the jaws 110 are moved against the biasing force of the biasing element 130 from a closed position (as illustrated in FIG. 2) to an open position (such as illustrated in FIG. 3).

The biasing element 130 may be held in place with respect to the respective shanks 114 of the jaw members 110a, 110b and may exert a closing force on the jaw members 110a, 110b to return the jaws 110 to a closed configuration. In the example of an embodiment of a tissue-engagement member 100 illustrated in FIGS. 2 and 3, a groove and/or shoulders 118 are provided on at least one of the shanks 114 of the jaw members 110a, 110b to hold the biasing element 130 in place with respect to the shanks 114 and the cam mechanism 150. However, other configurations are in the scope and spirit of the present disclosure. When a proximal force is no longer applied to the actuation element 122 (e.g., the actuation element 122 is released), the biasing force of the biasing element 130 biases the jaws 110 to return to the closed configuration, and the cam follower 154 rides along the cam surface 152 to move the actuator 120 proximally (e.g., from a position as in FIG. 3 to a position as in FIG. 2).

Although the example of an embodiment of a tissue-engagement member 100 illustrated in FIGS. 2-4 has a biasing element 130 which is separately formed from the cam mechanism 150 and the jaws 110 and the actuator 120 of the tissue-engagement member 100, and is provided around or about the exterior of the jaws 110, other configurations and positions and locations of a biasing element used in conjunction with a cam mechanism and/or jaws and/or an actuator of a tissue-engagement member are within the scope and spirit of the present disclosure. Moreover, other mechanisms for coupling jaws of a tissue-engagement member with an actuator to effect movement of the jaws between open and closed configurations are within the scope and spirit of the present disclosure. Various alternative embodiments are illustrated in FIGS. 5-18 as described in further detail below.

An alternative example of an embodiment of a tissue-engagement member 200 is illustrated in FIGS. 5-7 with different configurations of a cam mechanism 250 and a biasing element 230 than the configurations of a cam mechanism 150 and biasing element 130 illustrated in the tissue-engagement member 100 of FIGS. 2-4. It will be appreciated that for the sake of brevity and convenience, and without intent to limit, common elements with common functions in the tissue-engagement member 200 illustrated in FIGS. 5-7 as in the tissue-engagement member 100 illustrated in FIGS. 2-4 are indicated with the same reference characters differing in value by 100, reference being made to the above descriptions of similar elements and operations.

In general, the cam mechanism 250 of the tissue-engagement member 200 of FIGS. 3-5 may be considered similar to the cam mechanism 150 of the tissue-engagement member 200 of FIGS. 3-5 in that both cam mechanisms include a cam surface and a cam follower. However, the positions of such cam mechanism elements with respect to the jaws and actuator in the tissue-engagement member 200 are reversed from the positions of such elements in the tissue-engagement member 100. As may be appreciated with reference to FIG. 7, the cam surface 252 of the cam mechanism 250 is in the form of a slot formed in the actuator 220. The cam follower 254 is in the form of a pin extending inwardly towards the actuator 220 from the shanks 214 of the jaws 210, as may be seen partially in FIG. 5, and in phantom in FIG. 6 and FIG. 7.

As in the embodiment of a tissue-engagement member 100 illustrated in FIGS. 2-4, a biasing element 230 is used in conjunction with the cam mechanism 250 of the example of a tissue-engagement member 200 illustrated in FIGS. 5-7 to facilitate opening and closing of the jaws 210. However, in contrast, the biasing element 230 operatively engages the actuator 220, instead of being operatively engaged with the jaws 210 (as is the biasing element 130 of the tissue-engagement member 100 illustrated in FIGS. 2-4). Moreover, the biasing element 230 may be operatively engaged with (e.g., mounted on or formed as a part of) the housing 240 to extend from the housing 240 towards the cam mechanism 250. In the example of an embodiment illustrated in FIGS. 5-7, the biasing element 230 extends from a proximal end 243 of the housing 240 distally towards the distal end 201 of the tissue-engagement member 200. The proximal end 233 of the biasing element 230 may be coupled to or formed integrally with the proximal end 243 of the housing 240. A spring arm 232 may be formed along the distal end 231 of the biasing element 230 to interact with the actuator 220, as will be described in further detail below. As such, it will be appreciated that the housing 240 of the tissue-engagement member 100 illustrated in FIGS. 3-5 differs somewhat from the housing 140 of the tissue-engagement member 100 illustrated in FIGS. 2-4.

Other than the above-described differences, the other elements of the example of an embodiment of a tissue-engagement member 200 illustrated in FIGS. 5-7 are similar to corresponding elements of the example of an embodiment of a tissue-engagement member 100 illustrated in FIGS. 2-4. Moreover, operations of these tissue-engagement members are similar in that actuation of the tissue-engagement members to shift between closed and open configurations may be achieved by pulling, generally longitudinally, on an actuation element which is readily graspable by a medical instrument. In particular, a medical instrument (such as illustrated in FIG. 1 and FIGS. 19-21, as described in further detail below) may be used to move the actuation element 222 longitudinally along the longitudinal axis LA in a proximal direction (in a direction towards the proximal end 203 and away from the distal end 201 of the tissue-engagement member 200). The actuation element 222 is coupled to the actuator 220 via a shaft 224. Optionally, a shaft extension 226 (e.g., in the form of a wire 226) may couple the actuation element 222 with the shaft 224 (in any known or heretofore known manner, such as by brazing, welding, crimping, co-molding, passing of shaft extension 226 through a passage within shaft 224, etc.). In some embodiments, the actuation element 222 and the shaft extension 226 are formed from a common element (e.g., a wire with a proximal loop forming the actuation element 222). The shaft 224 (and/or the shaft extension 226 if provided) extends proximally through an axial opening 247 at the proximal end 243 of the housing 240 to be coupled with the actuation element 222. Proximal shifting of the actuation element 222 and shaft 224 cause proximal movement of the actuator 220. As the actuator 220 moves proximally, the cam followers 254 (on the shanks 214 along the proximal ends 213 of the jaws 210) ride along the cam surface 252 (formed in the actuator 220) to cause the jaw members 210a, 210b to pivot with respect to each other about the pivot pin 216 to shift the tissue-engaging ends 212 to move apart from a closed configuration (FIG. 6) to an open configuration (FIG. 7). Also, as the actuator 220 moves proximally to actuate the jaws 210, the actuator 220 moves proximally with respect to the biasing element 230. A shoulder 228 on the actuator 220, facing towards the proximal end 223 of the actuator 220, may engage with the biasing element 230 to shift the biasing element 230 to a biasing configuration in which the spring arm 232 is biased to an open configuration, storing potential energy, such as illustrated in FIG. 7. Thus, upon release of the actuation element 222, the potential energy stored in the biasing element 230 causes the spring arm 232 to release the stored potential energy, and to shift the actuator 220 distally to return the tissue-engaging ends 212 to a closed configuration (e.g., with the distal end 211 of the jaws 110 positioned to engage or hold tissue therebetween, such as illustrated in FIG. 1 or FIG. 6).

In another example of a tissue-engagement member 300, illustrated in FIGS. 8-10, a cam mechanism 350 similar to the cam mechanism 250 of the tissue-engagement member 200 illustrated in FIGS. 5-7, may be provided with a variation to the biasing element 330 interacting therewith. Although the biasing element 330 of the tissue-engagement member 300 illustrated in FIGS. 5-7 is operatively engaged with the actuator 320 as well as the housing 340 (similar to the biasing element 230 of the tissue-engagement member 200 being operatively engaged with the actuator 220 and the housing 240), the biasing element 330 is formed separately from the housing 340. More particularly, the biasing element 330 is positioned between the housing 340 and the actuator 320, such as in a window 345 in the housing 340. In the illustrated embodiment, the biasing element 330 is positioned about a shaft 324 extending proximally (towards the proximal end 303 of the tissue-engagement member 300) from the actuator 320, and may be in the form of a coil spring.

The example of an embodiment of a tissue-engagement member 300 illustrated in FIGS. 8-10 is actuated to shift the jaws 310 thereof between closed and open configurations in a manner similar to that in which the tissue-engagement member 200 illustrated in FIGS. 5-7 is actuated. The actuation element 322 may be shifted along the longitudinal axis LA of the tissue-engagement member 300 in a proximal direction (in a direction towards the proximal end 303 and away from the distal end 301 of the tissue-engagement member 300). The actuation element 322 is coupled to the actuator 320 via a shaft 324 extending proximally from the actuator 320. Optionally, a shaft extension 326 (e.g., in the form of a wire 326, as in the embodiment of FIGS. 5-7) extends through an axial opening 347 at the proximal end 343 of the housing 340 to couple the shaft 324 and the actuation element 322. Proximal shifting of the actuation element 322 and shaft 324 (and optional shaft extension 326) causes proximal movement of the actuator 320. As the actuator 320 moves proximally, the cam followers 354 (on the shanks 314 along the proximal ends 313 of the jaws 310) ride along the cam surface 352 (formed in the actuator 320) to cause the jaw members 310a, 310b to pivot with respect to each other about the pivot pin 316 to shift the tissue-engaging ends 312 to move apart from a closed configuration (FIG. 8 and FIG. 9) to an open configuration (FIG. 10). Also, as the actuator 320 moves proximally, the actuator 320 compresses the biasing element 330, storing potential energy therein, such as illustrated in FIG. 10. More particularly, as illustrated in FIG. 8, the distal end 331 of the biasing element 330 abuts against a shoulder 328 along the actuator 320 facing toward the proximal end 303 of the tissue-engagement member 300, and a proximal end 333 of the biasing element 330 abuts against a shoulder 348 on the housing 340 facing toward the distal end 301 of the tissue-engagement member 300 as the actuator 320 is shifted proximally. Upon release of the actuation element 322, the potential energy stored in the biasing element 330 causes the biasing element 330 to return to its uncompressed configuration (as in FIG. 9), shifting the actuator 320 distally to return the tissue-engaging ends 312 to a closed configuration (e.g., with the distal ends 311 of the jaws 310 positioned to engage or hold tissue therebetween, such as illustrated in FIG. 1 or FIG. 9).

Yet another modification to a biasing element 430 which may be used with a tissue-engagement member having elements similar to the tissue-engagement members 200, 300 of FIGS. 5-7 and FIGS. 8-10, respectively, is illustrated in the example of a tissue-engagement member 400 of FIGS. 11-13. Instead of being operatively engaged with an actuator 420 (as in the tissue-engagement members 200, 300 of FIGS. 5-7 and FIGS. 8-10), the biasing element 430 of the tissue-engagement member 400 illustrated in FIGS. 11-13 is operatively engaged with the jaws 410 of the tissue-engagement member 400. The illustrated biasing element 430 may be similar to the biasing element 130 of the tissue-engagement member 100 illustrated in FIGS. 2-4, with other elements being similar to the elements of the tissue-engagement members 200, 300 of FIGS. 5-7 and FIGS. 8-10, respectively. For the sake of brevity and convenience, and without intent to limit, common elements with common functions in the tissue-engagement member 400 illustrated in FIGS. 11-13 as in the tissue-engagement members 200, 300 illustrated in FIGS. 5-7 and FIGS. 8-10, respectively, are indicated with the same reference characters differing in value by 100, reference being made to the above descriptions of similar elements and operations.

As noted above, the biasing element 430 of the tissue-engagement member 400 illustrated in FIGS. 11-13 is operatively engaged with the jaws 410 of the tissue-engagement member 400, like the biasing element 130 of the tissue-engagement member 100 illustrated in FIGS. 2-4, to hold the jaws 410 in a closed configuration. However, instead of being operatively engaged with jaw shanks and/or a housing (as in the tissue-engagement member 100 of FIGS. 2-4), the biasing element 430 is operatively engaged with the tissue-engaging ends 412 of the jaws 410. More particularly, the biasing element 430 may be positioned about the tissue-engaging ends 412 of the jaws 410 (e.g., surrounding the jaws 410) to exert a biasing force to hold the jaws 410 in a closed configuration as illustrated in FIG. 11 and FIG. 12. In the example of an embodiment of a tissue-engagement member 400 illustrated in FIGS. 11-13, a groove and/or shoulders 418 are provided on at least one of the tissue-engaging ends 412 of the jaw members 410a, 410b to hold the biasing element 430 in place with respect to the jaws 410. However, other configurations are in the scope and spirit of the present disclosure.

Actuation of the example of an embodiment of a tissue-engagement member 400 illustrated in FIGS. 11-13 is similar to that of the tissue-engagement members 200, 300 illustrated in FIGS. 5-7 and 8-10, other than the location of the biasing force returning the jaws 410 to a closed configuration. The actuation element 422 along the proximal end 403 of the tissue-engagement member 400 may be shifted along the longitudinal axis LA of the tissue-engagement member 400 in a proximal direction (in a direction towards the proximal end 403 and away from the distal end 401 of the tissue-engagement member 400) to shift an actuator 420 operatively associated with the jaws 410 to shift the jaws 410 between a closed configuration (as in FIGS. 11 and 12) and an open configuration (as in FIG. 13).

The actuation element 422 is coupled to the actuator 420 via a shaft 424 extending proximally from the actuator 420. Optionally a shaft extension 426 (e.g., in the form of a wire 426, as in the embodiment of FIGS. 5-7) extends proximally through an axial opening 447 at the proximal end 443 of the housing 440 to couple the shaft 424 and the actuation element 422. Proximal shifting of the actuation element 422 causes proximal shifting of the actuator 420. As the actuator 420 moves proximally, the cam followers 454 (on the shanks 414 along the proximal ends 413 of the jaws 410) ride along the cam surface 452 (formed in the actuator 420) to cause the jaw members 410a, 410b to pivot with respect to each other about the pivot pin 416 to shift the tissue-engaging ends 412 to move apart from a closed configuration (FIG. 11 and FIG. 12) to an open configuration (FIG. 13). As the jaws 410 open, the biasing element 430 is stretched, storing potential energy therein, such as illustrated in FIG. 13. Upon release of the actuation element 422, the potential energy stored in the biasing element 430 causes the biasing element 430 to return to its uncompressed configuration (as in FIG. 12), moving the tissue-engaging ends 412 to a closed configuration (e.g., with the distal ends 411 of the jaws 410 positioned to engage or hold tissue therebetween, such as illustrated in FIG. 1 or FIG. 11 or FIG. 12).

In another embodiment of a tissue-engagement member 500 formed in accordance with various principles of the present disclosure, and as illustrated in FIGS. 14-18, the jaws 510 may be configured or formed to be naturally biased into an open configuration (as in FIGS. 14, 15, 17, and 18). The actuator 520 may be in the form of a retention member or fillet, shiftable to retain the jaws 510 in a closed configuration (as in FIG. 16) or to allow the jaws 510 to expand into the open configuration (as in FIGS. 14, 15, 17, and 18). The biasing element 530 may be in the form of a spring-biased collet or boss or solid spring (e.g., conical solid spring) with a spring opening 532 operatively engaging the actuator 120 to bias the actuator 520 to return to a configuration closing the jaws 510. Details of the example of an embodiment of a tissue-engagement member 500 illustrated in FIG. 14 may be appreciated with reference to the cross-sectional view illustrated in FIG. 15 along line XV-XV of FIG. 14, and the elevational views illustrated in FIG. 16 and FIG. 17 with the actuator 520 in phantom.

In the embodiment illustrated in FIG. 15, the jaws 510 of the illustrated tissue-engagement member 500 have jaw members 510a, 510b (between which tissue may be grasped when the jaws 510 are in a closed configuration) adjacent the distal end 511 of the jaws 110 with shanks 514 extending proximally towards the proximal end 513 of the jaws 510 at which the shanks 514 are coupled via a jaw ball joint 516. The shanks 514 are configured to bias the jaw members 510a, 510b apart when unconstrained. The actuator 520 is positioned relative to the jaws 510 and relative to the biasing element 530 to retain the jaws 510 in a closed configuration, as illustrated in FIG. 16. To open the jaws 510, an actuation element 522, which may be similar to the above-described actuation elements 122, 222, 322, 422 (reference being made to details of such actuation elements described above as being optionally applicable to the actuation element 522), is shifted along the longitudinal axis LA in a proximal direction (in a direction towards the proximal end 503 of the tissue-engagement member 500 and away from the distal end 501 of the tissue-engagement member 500). The actuation element 522 is coupled to the actuator 520 via a shaft 524 coupled to a proximal end 523 of the actuator 520 (and extending through an opening 537 in the proximal end 533 of the biasing element 530 as well as an opening 517 through the jaw ball joint 516 of the jaws 510). Proximal shifting of the actuation element 522 and the shaft 524 shift the actuator 520 proximally towards the spring opening 532 along the distal end 531 of the biasing element 530 so that the actuator 520 biases the spring opening 532 into an expanded tensioned configuration, storing potential energy. The interaction between the actuator 520 and the spring opening 532 of the biasing element 530 may be considered a camming action such that the tissue-engagement member 500 may be considered to have a cam mechanism operatively associated with the actuator 520 and the biasing element 530. Upon release of the actuation element 522, the potential energy stored in the spring opening 532 of the biasing element 530 causes the spring opening 532 to return to its rest configuration, shifting the actuator 520 distally over the shank 514 of the jaws 510 to return the tissue-engaging ends 512 to a closed configuration (e.g., with the distal ends 511 of the jaws 510 positioned to engage or hold tissue therebetween), such as illustrated in FIG. 1 or FIG. 16.

A modified version of a tissue-engagement member 500 as in FIGS. 14-17 is illustrated in FIG. 18. The modified tissue-engagement member 500' of FIG. 18 has a modified biasing element 530' in which the spring opening 532' includes cuts or slits 535' along the distal end 531' thereof to facilitate expansion of the spring opening 532' as the actuator 520 extends proximally into the spring opening 532' upon shifting the actuator 520 and shaft 524 proximally along the longitudinal axis LA (toward the proximal end 503 and away from the distal end 501 of the tissue-engagement member 500). It will be appreciated that the remaining elements of the tissue-engagement member 500' illustrated in FIG. 18 are substantially the same as similarly labeled elements of the tissue-engagement member 500 illustrated in FIGS. 14-17, reference being made to the above descriptions of such elements as applicable to the embodiment of FIG. 18.

Reference is made to FIG. 1 and FIGS. 19-20 to describe deployment of a tissue-engagement member formed in accordance with various principles of the present disclosure. It will be appreciated, in view of the above, that any of the above-described tissue-engagement members 200, 300, 400, 500, 500' may be deployed in a similar manner. In the example illustrated in FIG. 1, more than one tissue-engagement member 100 may be deployed in a similar manner with a tether 160 extending between the tissue-engagement members 100. The tether 160 may be a tissue traction element configured to apply traction to tissue T engaged by the first-deployed of the tissue-engagement members 100 (on the left in FIG. 1) upon engaging the second-deployed of the tissue-engagement members 100 (on the right in FIG. 2) with tissue spaced apart from the first-engaged tissue-engagement member 100. It will be appreciated that other uses and environments for a tissue-engagement member formed in accordance with various principles of the present disclosure are within the scope and spirit of the present disclosure.

In accordance with an aspect of the present disclosure, a tissue engagement system includes one or more tissue-engagement members 100 and a tissue-engagement-member manipulator 170 configured to actuate at least one of the tissue-engagement members 100, as illustrated in FIG. 1. One or more tissue-engagement members 100 may be deployed to a deployment site, optionally along with the manipulator 170 (e.g., in the same delivery device). Optionally, the manipulator 170 is deployed with a manipulator deployment system 180 configured to deliver as well as to maneuver the manipulator 170 to actuate the tissue-engagement member 100. It will be appreciated that the term maneuver and conjugations thereof is used for the sake of convenience without intent to limit, and may be used interchangeably herein with terms such as manipulate, move, control, actuate, steer, navigate, etc., including various conjugations thereof. For the sake of simplicity, the deployment system with which the tissue-engagement members 100 and/or manipulator 170 and the deployment system 180 are deployed is not shown. It will be appreciated that any known or heretofore known deployment system may be used, such as any of a variety of flexible tubular elements, typically with optical/visualization capabilities (e.g., an endoscope or other introducer), the details of such system not being critical to the principles of the present disclosure. The tissue-engagement members 100 and manipulator 170 and deployment system 180 may be navigated to/deployed at a deployment site via separate systems (e.g., separate delivery systems) or separate working channels in a common system. The present disclosure is not limited in this context.

As illustrated in FIG. 1, the manipulator 170 is extended out the distal end 181 of the manipulator deployment system 180 to engage the actuation element 122 of a tissue-engagement member 100. An actuator-engaging element 172 is provided along a distal end 171 of the manipulator 170 to operatively engage an actuation element 122 so that proximal shifting of the manipulator 170 pulls the actuation element 122 proximally to actuate the tissue-engagement member 100 to open in a manner as described above. In accordance with an aspect of the present disclosure, the actuator-engaging element 172 is configured to operatively engage the actuation element 122 of the tissue-engagement member 100 within a range of angular orientations with respect to the actuation element 122. In other words, the configurations of the actuation element 122 and the actuator-engaging element 172 allow for a range of relative positions with respect to each other which still allow for operative engagement therebetween. In some embodiments, the actuator-engaging element 172 is in the form of a hook (such as formed along a distal end of a pull wire) which is engaged with the actuation element 122, such as by being inserted into an opening 125 within the actuation element 122. As may be appreciated by those of ordinary skill in the art, the hook (generally, along a major plane in which a majority of the hook lies) merely needs to be transverse (i.e., not parallel) to the actuation element 122 (generally, the major plane in which the actuation element 122 lies, or at least the portion of the actuation element 122 to be grasped by the actuator-engaging element 172 of the manipulator 170). As such, a range of relative orientations of the actuator-engaging element 172 and the actuation element 122 allow operative engagement therebetween to allow movement of the manipulator 170 to effect movement of the actuation element 122. More particularly, the actuator-engaging element 172 may be up to just a few degrees short of 90° (as may generally be determined by the thickness of the actuator-engaging element 172, such as about 5°), or just a few degrees short of 270° to allow the actuator-engaging element 172 to grab and remain engaged with the actuation element 122 (as may generally be determined by the thickness of the actuator-engaging element 172, such as about 5°), from an ideally aligned position with the hook substantially perpendicular to the actuation element 122 with the open side of the hook oriented to hook over a portion of the actuation element 122.

In the example of an embodiment of a deployment system 180 illustrated in FIG. 1, a flexible elongate element 174 of the manipulator 170 extends proximally along a flexible tubular element 182, such as through a lumen 185 (partially shown, in phantom) within the flexible tubular element 182, to be controlled at a proximal end 183 of the deployment system 180 by a medical professional, such as via a control handle 190. The flexible tubular element 182 may be a catheter or other element with a lumen 185 therein, prefer- ably capable of being navigated through a body passage or body lumen (e.g., through the gastrointestinal system), such as known or heretofore known in the art. The flexible tubular element 182 may include a coil section (with the lumen 185 extending therethrough) to facilitate transluminal navigation through tortuous pathways, such as known in the art. A sheath 184 may extend over the length of the flexible tubular element 182.

In the example of an embodiment of a control handle 190 illustrated in FIG. 1, a rotating knob 192 coupled with the flexible elongate element 174 of the manipulator 170 may be used to rotate the actuator-engaging element 172 of the manipulator 170 for positioning with respect to the actuation element 122 to operatively engage the actuation element 122.

Once the actuator-engaging element 172 and the actuation element 122 are operatively engaged (such as illustrated in FIG. 1), the manipulator 170 may be retracted proximally to retract the actuator 120 of the tissue-engagement member 100 proximally. For instance, the control handle 190 may include a translating knob 194 axially translatable along the control handle 190 (in a direction between the proximal end 183 and the distal end 181 of the deployment system 180) to move the manipulator 170 distally or proximally. In the example illustrated in FIG. 19 (showing the tissue engage- ment system enlarged relative to the depictions of FIG. 20 and FIG. 21, but without illustrating the control handle 190), the tissue-engagement member 100 is proximally retracted by the manipulator 170 to engage the proximal end 143 of the housing 140 of the tissue-engagement member 100 with a distal section 186 at a distal end 181 of the flexible tubular element 182. In some embodiments, the flexible tubular element 182 is flexible, such as formed from a coil element (such as described above), and the distal section 186 is less flexible than the portions of the flexible tubular element 182 proximal thereto. For instance, the distal section 186 may be tubular element, such as a bushing, without the springy resiliency and potential axial mobility of the portions of the flexible tubular element 182 extending proximally there- from. The manipulator 170 may be retracted into the lumen 185 of the flexible tubular element 182 and the distal section 186, but the tissue-engagement member 100 does not fit within the lumen 185, as may be appreciated with reference to FIG. 19. Instead, the distal end of the distal section 186 provides a shoulder 188 against which the proximal end 143 of the housing 140 of the tissue-engagement member 100 abuts when moved proximally toward the deployment sys- tem 180. Such arrangement allows for relative longitudinal movement of the manipulator 170 with respect to the housing 140 of the tissue-engagement member 100.

An alignment sheath 184 may be distally extended (such as by being axially shifted at a proximal end thereof manu- ally or via an associated controller, such as a control handle or control knob) over the housing 140 of the tissue-engage- ment member 100 to hold the tissue-engagement member 100 in place relative to the deployment system 180, as illustrated in FIG. 20. With the housing 140 held against relative movement with respect to the flexible tubular ele- ment 182, proximal retraction of the manipulator 170 rela- tive to the flexible tubular element 182 allows the manipu- lator 170 to pull the actuator 120 relative to the housing 140 of the tissue-engagement member 100. The translating knob

194 may be moved proximally with respect to the flexible tubular element 182 to effect proximal movement of the flexible elongate element 174 (shown in phantom extending through the flexible tubular element 182 and sheath 184). The actuation element 122 and the shaft 124 (extending proximally from the actuator 120) may fit within the lumen 185 of the flexible tubular element 182 to allow the actuator 120 to move proximally relative to the housing 140. In a manner as described above, proximal shifting of the actuator 120 relative to the jaws 110 (which are pivotably coupled to the housing 140 and thus held with the housing 140 against proximal movement) causes the jaws 110 to shift to an open configuration such as illustrated in FIG. 21. Reference is made above to further details of shifting of the actuator 120 causing the cam followers 154 on the actuator 120 to ride along the cam surfaces 152 on the respective shanks 114 of the jaws 110 to shift the jaws 110 to an open configuration, relevant reference numerals being provided in FIGS. 19-21 for referencing with respect to the above descriptions of actuation of the jaws 110.

It will be appreciated that various structures and features of the embodiments described herein and illustrated in the figures have several separate and independent unique ben- efits. Therefore, the various structures and features described herein need not all be present in order to achieve at least some of the desired characteristics and/or benefits described herein. Moreover, the various features described herein may be used singly or in any combination. It will be appreciated that various features described with respect to one embodi- ment may be applied to another embodiment, whether or not explicitly indicated. Thus, it should be understood that one or more of the features described with reference to one embodiment can be combined with one or more of the features of any of the other embodiments described herein. That is, any of the features described herein can be mixed and matched to create hybrid designs, and such hybrid designs are within the scope of the present disclosure. Therefore, the present invention is not limited to only the embodiments specifically described herein. The above descriptions are of illustrative examples of embodiments only, and are not intended as limiting the broader aspects of the present disclosure.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without depart- ing from the concept, spirit, or scope, or characteristics thereof. For example, various features of the disclosure are grouped together in one or more aspects, embodiments, or configurations for the purpose of streamlining the disclo- sure. However, it should be understood that various features of the certain aspects, embodiments, or configurations of the disclosure may be combined in alternate aspects, embodi- ments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A tissue-engagement member comprising:
    a pair of jaw members pivotably coupled together about a pivot point and each pivotable between a closed configuration with distal ends thereof engaging each other to grasp tissue against surfaces of the jaw members facing each other, and an open configuration with the distal ends spaced apart from each other to receive tissue between the jaws or to release tissue from between the jaws;
    an actuator operatively engaged with said pair of jaw members to shift said jaw members between the closed configuration and the open configuration;
    a biasing element encircling the exterior of a portion of at least one of said jaw members or a distal portion of said actuator to cause said jaw members to be biased into the closed configuration; and
    a cam mechanism proximal to the pivot point and operatively associated with at least one of said actuator, said biasing element, or at least one of said jaw members and including a first cam element movable with respect to a second cam element to shift said jaw members between the closed configuration and the open configuration.

2. The tissue-engagement member of claim 1, wherein said actuator is shiftable against the force of said biasing element to shift said jaw members from the closed configuration to the open configuration.

3. The tissue-engagement member of claim 2, wherein said biasing element operatively engages at least one of said actuator or at least one of said jaw members.

4. The tissue-engagement member of claim 1, wherein said cam mechanism comprises a cam surface on one of said actuator or at least one of said jaw members.

5. The tissue-engagement member of claim 4, wherein said cam mechanism further comprises a cam follower on the other of said actuator or at least one of said jaw members.

6. The tissue-engagement member of claim 4, wherein said biasing element operatively engages one of said actuator or at least one of said jaw members to actuate said cam mechanism to return said jaw members to a closed configuration from an open configuration.

7. The tissue-engagement member of claim 1, further comprising a housing, said jaw member and said actuator positioned within a portion of said housing.

8. The tissue-engagement member of claim 7, wherein said biasing element operatively engages one of said actuator or said housing or at least one of said jaw members to bias said jaw members to a closed configuration.

9. The tissue-engagement member of claim 1, wherein said biasing element biases said actuator to hold said jaw members in the closed configuration.

10. The tissue-engagement member of claim 1, further comprising an actuation element coupled to said actuator and graspable to move said actuation element to shift said jaw members between the closed and open configurations.

11. A tissue-engagement member comprising:
    a pair of jaw members pivotably coupled together about a pivot and pivotable between a closed configuration and an open configuration;
    an actuator operatively engaged with said pair of jaw members to shift said jaw members between the closed configuration and the open configuration; and

23 a biasing element positioned proximal to the pivot and encircling the exterior of a portion of at least one of said jaw members or a distal portion of said actuator to cause said jaw members to be biased into the closed configuration.

12. The tissue-engagement member of claim 11, wherein said biasing element is an elastic element positioned about said jaw members.

13. The tissue-engagement member of claim 11, wherein said biasing element encircles a distal portion of said actuator.

14. The tissue-engagement member of claim 11, further comprising a cam mechanism operatively associated with at least one of said actuator, said biasing element, or at least one of said jaw members.

15. The tissue-engagement member of claim 14, wherein said cam mechanism comprises a cam surface on one of said actuator or at least one of said jaw members.

16. The tissue-engagement member of claim 15, wherein said cam mechanism further comprises a cam follower on the other of said actuator or at least one of said jaw members.

17. A tissue-engagement system comprising:

a tissue-engagement member having a distal end and a proximal end, said tissue-engagement member comprising jaws along the distal end pivotably coupled about a pivot point, an actuator along the proximal end, and a biasing element positioned proximal to the pivot point and encircling the exterior of a portion of at least one of said jaws or a distal portion of said actuator, wherein said jaws are shiftable between a closed configuration and an open configuration, said actuator is operatively engaged with said jaws via a cam mechanism to move said jaws between the closed and open configurations, and said biasing element shifts configurations as said jaws shift between the closed and open configurations and biases said jaws into the closed configuration; a tissue-engagement-member manipulator having a distal end configured to operatively engage with said tissue-engagement member to move said actuator axially to shift said jaws between the closed and open configurations; and a manipulator deployment system configured to deliver and to maneuver said tissue-engagement-member manipulator to move said actuator.

18. The tissue-engagement system of claim 17, wherein:

an actuation element in the form of a loop is operatively coupled with a proximal end of said actuator along the proximal end of said tissue-engagement member; and an actuator-engagement element is provided on a distal end of said tissue-engagement-member manipulator and configured to engage with said actuation element in a range of orientations with respect to said actuation element.

19. The tissue-engagement system of claim 17, wherein said manipulator deployment system further comprises a flexible tubular element with a lumen defined therethrough, and a sheath, wherein said tissue-engagement-member manipulator is movable proximally into the lumen defined through said flexible tubular element to bring the proximal end of said tissue-engagement member into abutment with a distal end of said flexible tubular element, and said sheath is movable over the distal end of said flexible tubular element and over said tissue-engagement member to hold said tissue-engagement member in alignment with said manipulator deployment system.

* * * * *